United States Patent [19]

Arita et al.

[11] Patent Number: 5,478,838

[45] Date of Patent: Dec. 26, 1995

[54] 4-AMINO(ALKYL)CYCLOHEXANE-1-CARBOXAMIDE COMPOUND AND USE THEREOF

[75] Inventors: Masafumi Arita; Tadamasa Saito, both of Iruma; Hirofumi Okuda, Fukuoka; Hiroyuki Sato; Masayoshi Uehata, both of Iruma, all of Japan

[73] Assignee: Yoshitomi Pharmaceutical Industries, Ltd., Osaka, Japan

[21] Appl. No.: 204,211

[22] PCT Filed: Sep. 4, 1992

[86] PCT No.: PCT/JP92/01139

§ 371 Date: Mar. 7, 1994

§ 102(e) Date: Mar. 7, 1994

[87] PCT Pub. No.: WO93/05021

PCT Pub. Date: Mar. 18, 1993

[30] Foreign Application Priority Data

Sep. 6, 1991 [JP] Japan ..................................... 3-255689
May 12, 1992 [JP] Japan ..................................... 4-146175

[51] Int. Cl.⁶ ...................... A61K 31/435; C07D 471/04
[52] U.S. Cl. ......................... 514/300; 514/303; 546/113; 546/119
[58] Field of Search ..................... 546/113, 119; 514/300, 303

[56] References Cited

U.S. PATENT DOCUMENTS 4,997,834 3/1991 Muro et al. ........................ 514/227.8

FOREIGN PATENT DOCUMENTS 0370498 5/1990 European Pat. Off. .

OTHER PUBLICATIONS

Muro et al., "Preparation of (Pyridylcarbamoyl)Cyclohexane Derivatives As Antihypertensive Agents", Chemical Abstracts, vol. 116, No. 15, 1992, Abstract No. 151571b.

CIP Abstract 89–110631/15 (corresponding to JP–A–64–56661) (1989).

Primary Examiner—Bernard Dentz
Attorney, Agent, or Firm—Wenderoth, Lind & Ponack

[57] ABSTRACT

4-Amino(alkyl)cyclohexane-1-carboxamide compounds of the formula (I)

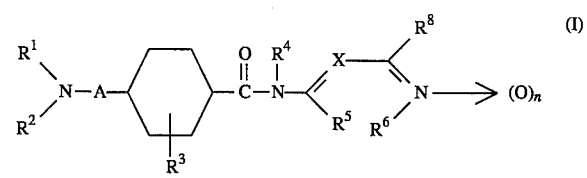

wherein each symbol is as defined in the Specification, isomers thereof and pharmaceutically acceptable acid addition salts thereof.

The 4-amino(alkyl)cyclohexane-1-carboxamide compounds, isomers thereof and pharmaceutically acceptable acid addition salts thereof of the present invention have potent and long-lasting coronary, cerebral, renal and peripheral blood flow increasing actions and are less toxic, and thus are useful as a potent and long-lasting antihypertensive agent and an agent for the prevention and treatment of diseases in the circulatory organs such as coronary, cerebral, renal and peripheral arteries. Moreover, the compounds of the present invention exhibit inhibitory action on experimental asthma of guinea pigs, which is caused by histamine inhalation, and inhibitory action on contraction of trachea strips isolated from guinea pigs, which is caused by acetylcholine, and thus are useful as therapeutic agents for asthma.

10 Claims, No Drawings

4-AMINO(ALKYL)CYCLOHEXANE-1-CARBOXAMIDE COMPOUND AND USE THEREOF

This application is a 371 of PCT/JP92/01139 filed Sep. 4, 1992.

1. Technical Field

The present invention relates to novel and pharmaceutically useful 4-amino(alkyl)cyclohexane-1-carboxamide compounds, isomers thereof and pharmaceutically acceptable acid addition salts thereof.

2. Background Art

It is known that one of the causes of hypertensions and coronary or cerebral circulatory diseases, which constitute a major social problem as adult diseases, is the abnormal contraction of smooth muscles, which is caused by a rise in intracellular concentrations of calcium ion. The rise of the intracellular concentrations of calcium ion is caused, for example, 1) through the membrane potential-dependent calcium channel, 2) by release of calcium from the intracellular organella where it is stored and 3) through the receptor-dependent channel, and therefore its origin is uneven. Further, it is recognized that the excessive calcium ions induce twitches of the coronary artery and the cerebrovascular artery and these vascular twitches constitute one of the causes of angina pectoris, myocardial infarction and cerebral infarction.

Incidentally, calcium antagonists have been recently employed for the treatment of hypertension or coronary, cerebral and peripheral circulatory diseases. While the calcium antagonists show antagonistic activity against the membrane potential-dependent calcium channel, they scarcely show antagonistic activities against other influx of calcium ion into the cell and liberation of calcium ion from the storage organella.

As compounds having intracellular calcium antagonistic action as well as inhibitory action against membrane potential-dependent smooth muscle contraction which conventional calcium antagonists inhibit, WO 90/05723 discloses that certain trans-4-amino(alkyl)-pyridylcarbamoylcyclohexane compounds, optical isomers thereof and pharmaceutically acceptable acid addition salts thereof have long-lasting coronary, cerebral and renal blood flow-increasing actions and are useful as an antihypertensive agent and an agent for the prevention and treatment of coronary, cerebral and renal circulatory diseases.

DISCLOSURE OF THE INVENTION

An object of the present invention is to provide a compound having a potent and long-lasting blood flow-increasing action in the coronary, cerebral, renal and peripheral arteries, which is less toxic than conventional compounds.

Under these circumstances, the present inventors have made intensive studies and found that 4-amino(alkyl)cyclohexane-1-carboxamide compounds, isomers thereof and pharmaceutically acceptable acid addition salts thereof can achieve the aforementioned objects, and completed the present invention.

Moreover, the compounds of the present invention exhibit inhibitory action on histamine inhalation-induced experimental asthma in guinea pig and acetylcholine-induced inhibitory action on contraction of extirpated guinea pig trachea, thus showing the anti-asthma action of the compound of the invention.

That is, the present invention relates to:

(1) 4-amino(alkyl)cyclohexane-1-carboxamide compounds of the formula (I)

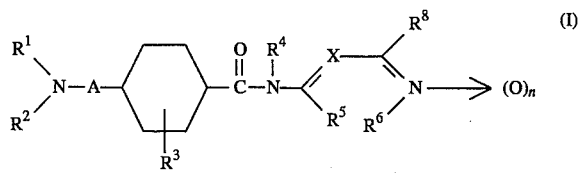

wherein:

$R^1$ and $R^2$ are the same or different and each is hydrogen, alkyl, or cycloalkyl, cycloalkylalkyl, phenyl, aralkyl, piperidyl or pyrrolidinyl, which may have substituent on the ring, or a group of the formula

[wherein; R is hydrogen, alkyl, —NR'R" (where R' and R" are the same or different and each is hydrogen, alkyl, aralkyl or phenyl), $R^0$ is hydrogen, alkyl, aralkyl, phenyl, nitro or cyano, or R and $R^0$ may combinedly form a heterocyclic ring which may have, in the ring, oxygen atom, sulfur atom or optionally substituted nitrogen atom], or $R^1$ and $R^2$ combinedly show alkylidene or phenylalkylidene, or $R^1$ and $R^2$ form, together with the nitrogen atom binding therewith, a heterocyclic ring which may have, in the ring, oxygen atom, sulfur atom or optionally substituted nitrogen atom;

$R^3$ and $R^4$ are each hydrogen or alkyl;

A is a single bond or alkylene;

X is $=C(R^7)-$ or $=N-$;

$R^5$ and $R^6$ together show a group of the formula

| —CRa=CRb— | (a), | —NRa—C(=Rb)— | (b), |
| —N=CRb— | (c), | —C(=Ra)—NRb— | (d), |
| —CRa=N— | (e) or | —NRa— | (f) |

[wherein; Ra and Rb are the same or different and each is hydrogen, halogen, alkyl, alkoxy, aralkyl, haloalkyl, nitro, —NRcRd (wherein Rc and Rd are the same or different and each is hydrogen, alkyl, —$COR^9$, —$COOR^{9'}$, —$SO_2R^{9'}$ (where $R^9$ is hydrogen, alkyl, phenyl or aralkyl and $R^{9'}$ is alkyl, phenyl or aralkyl), or Rc and Rd form, together with the nitrogen atom binding therewith, a heterocyclic ring which may have, in the ring, oxygen atom, sulfur atom or optionally substituted nitrogen atom), cyano, azide, optionally substituted hydrazino, —$COOR^{10}$, —$CONR^{11}R^{12}$ (wherein $R^{10-12}$ are each hydrogen, alkyl, phenyl or aralkyl), or Ra and Rb combinedly form an optionally hydrogenated 5- or 6-membered aromatic ring which may have at least one of nitrogen atom, sulfur atom and oxygen atom, provided that when $R^5$ and $R^6$ are of the formula (b) or (d), Ra and Rb unexceptionally together form an optionally hydrogenated 5- or 6-membered aromatic ring which may have at least one of nitrogen atom, sulfur atom and oxygen atom];

$R^7$ and $R^8$ are the same or different and each is hydrogen, halogen, alkyl, alkoxy, aralkyl, haloalkyl, nitro, —NReRf [wherein Re and Rf are the same or different and each is hydrogen, alkyl, —$COR^9$, —$COOR^{9'}$, —$SO_2R^{9'}$ (where $R^9$ is hydrogen, alkyl, phenyl or aralkyl and R⁹' is alkyl, phenyl or aralkyl), or Re and Rf form, together with the nitrogen atom binding therewith, a heterocyclic ring which may have, in the ring, oxygen atom, sulfur atom or optionally substituted nitrogen atom], cyano, azido, optionally substituted hydrazino, —COOR¹⁰, —CONR¹¹R¹² (wherein R¹⁰⁻¹² are each hydrogen, alkyl, phenyl or aralkyl); and n is 0 or 1; with the proviso that when R⁵ and R⁶ are of the formula (a), X is =C(R⁷)— and either one of Ra, Rb, R⁷ and R⁸ is —NRcRd, —NReRf, azido, optionally substituted hydrazino, —COOR¹⁰ or —CONR¹¹R¹², or Ra and Rb combinedly form an optionally hydrogenated 5- or 6-membered aromatic ring which may have, in the ring, at least one of nitrogen atom, sulfur atom and oxygen atom;

isomers thereof and pharmaceutically acceptable acid addition salts thereof, (2) 4-amino(alkyl)cyclohexane-1-carboxamide compounds of the above (1) having the formula (Ia)

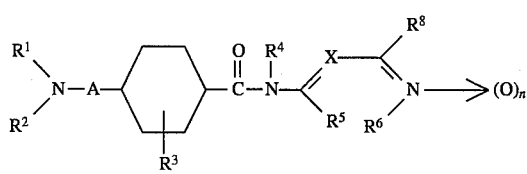

(Ia)

wherein:

R¹ and R² are the same or different and each is hydrogen, alkyl having 1 to 10 carbon atoms, or cycloalkyl having 3 to 7 carbon atoms, cycloalkylalkyl, phenyl, aralkyl, piperidyl or pyrrolidinyl which may have substituent on the ring, or R¹ and R² combinedly show alkylidene or phenylalkylidene, or R¹ and R² form, together with the nitrogen atom binding therewith, a heterocyclic ring which may have, in the ring, oxygen atom, sulfur atom or optionally substituted nitrogen atom;

R³ and R⁴ are each hydrogen or alkyl;

A is a single bond or alkylene;

X is =C(R⁷)— or =N—;

R⁵ and R⁶ together show a group of the formula

| —CRa=CRb— | (a), | —NRa—C(=Rb)— | (b), |
| —N=CRb— | (c), | —C(=Ra)—NRb— | (d), |
| —CRa=N— | (e) or | —NRa— | (f) |

[wherein; Ra and Rb are the same or different and each is hydrogen, halogen, alkyl, alkoxy, aralkyl, haloalkyl, nitro, —NRcRd (wherein Rc and Rd are the same or different and each is hydrogen, alkyl, —COR⁹, —COOR⁹', —SO₂R⁹' (where R⁹ is hydrogen, alkyl, phenyl or aralkyl and R⁹' is alkyl, phenyl or aralkyl), or Rc and Rd form, together with the nitrogen atom binding therewith, a heterocyclic ring which may have, in the ring, oxygen atom, sulfur atom or optionally substituted nitrogen atom), cyano, azido, optionally substituted hydrazino, —COOR¹⁰, —CONR¹¹R¹² (wherein R¹⁰⁻¹² are each hydrogen, alkyl, phenyl or aralkyl), or Ra and Rb combinedly form an optionally hydrogenated 5- or 6-membered aromatic ring which may have, in the ring, at least one of nitrogen atom, sulfur atom and oxygen atom, provided that when R⁵ and R⁶ are of the formula (b) or (d), Ra and Rb unexceptionally together form an optionally hydrogenated 5- or 6-membered aromatic ring which may have at least one of nitrogen atom, sulfur atom and oxygen atom];

R⁷ and R⁸ are the same or different and each is hydrogen, halogen, alkyl, alkoxy, aralkyl, haloalkyl, nitro, —NReRf [wherein Re and Rf are the same or different are each is hydrogen, alkyl, —COR⁹, —COOR⁹', or —SO₂R⁹' (where R⁹ is hydrogen, alkyl, phenyl or aralkyl and R⁹' is alkyl, phenyl or aralkyl), or Re and Rf form, together with the nitrogen atom binding therewith, a heterocyclic ring which may have, in the ring, oxygen atom, sulfur atom or optionally substituted nitrogen atom], cyano, azido, optionally substituted hydrazino, —COOR¹⁰, —CONR¹¹R¹² (wherein R¹⁰⁻¹² are each hydrogen, alkyl, phenyl or aralkyl); and n is 0 or 1; with the proviso that when R⁵ and R⁶ are of the formula (a), X is =C(R⁷)— and either one of Ra, Rb, R⁷ and R⁸ is —NRcRd, —NReRf, azido, optionally substituted hydrazino, —COOR¹⁰ or —CONR¹¹R¹², or Ra and Rb together form an optionally hydrogenated 5- or 6-membered aromatic ring which may have, in the ring, at least one of nitrogen atom, sulfur atom and oxygen atom;

isomers thereof and pharmaceutically acceptable acid addition salts thereof, (3) 4-amino(alkyl)cyclohexane-1-carboxamide compounds of the above (1) having the formula (Ib)

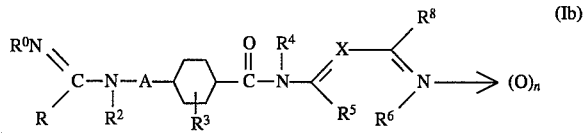

(Ib)

wherein:

R is hydrogen, alkyl or —NR'R" (wherein R' and R" are the same or different and each is hydrogen, alkyl, aralkyl or phenyl);

R⁰ is hydrogen, alkyl, aralkyl, phenyl, nitro or cyano, or R and R⁰ combinedly form a heterocyclic ring which may have, in the ring, oxygen atom, sulfur atom or optionally substituted nitrogen atom;

R² is hydrogen, alkyl or aralkyl;

R³ and R⁴ are each hydrogen or alkyl;

A is a single bond or alkylene;

X is =C(R⁷)— or =N—;

R⁵ and R⁶ together show a group of the formula

| —CRa=CRb— | (a), | —NRa—C(=Rb)— | (b), |
| —N=CRb— | (c), | —C(=Ra)—NRb— | (d), |
| —CRa=N— | (e) or | —NRa— | (f) |

[wherein; Ra and Rb are the same or different and each is hydrogen, halogen, alkyl, alkoxy, aralkyl, haloalkyl, nitro, —NRcRd (wherein Rc and Rd are the same or different and each is hydrogen, alkyl, —COR⁹, —COOR⁹', —SO₂R⁹' (where R⁹ is hydrogen, alkyl, phenyl or aralkyl and R⁹' is alkyl, phenyl or aralkyl), or Rc and Rd form, together with the nitrogen atom binding therewith, a heterocyclic ring which may have, in the ring, oxygen atom, sulfur atom or optionally substituted nitrogen atom), cyano, azido, optionally substituted hydrazino, —COOR¹⁰, —CONR¹¹R¹² (wherein R¹⁰⁻¹² are each hydrogen, alkyl, phenyl or aralkyl), or Ra and Rb combinedly form an optionally hydrogenated 5- or 6-membered aromatic ring which may have, in the ring, at least one of nitrogen atom, sulfur atom and oxygen atom, provided that when R⁵ and R⁶ are of the formula (b) or (d), Ra and Rb unexceptionally together form an optionally hydrogenated 5- or 6-membered aromatic ring which may have at least one of nitrogen atom, sulfur atom and oxygen atom];

$R^7$ and $R^8$ are the same or different and each is hydrogen, halogen, alkyl, alkoxy, aralkyl, haloalkyl, nitro, —NReRf [wherein Re and Rf are the same or different are each is hydrogen, alkyl, —$COR^9$, —$COOR^{9'}$ or —$SO_2R^{9'}$ (where $R^9$ is hydrogen, alkyl, phenyl or aralkyl and $R^{9'}$ is alkyl, phenyl or aralkyl), or Re and Rf form, together with the nitrogen atom binding therewith, a heterocyclic ring which may have, in the ring, oxygen atom, sulfur atom or optionally substituted nitrogen atom], cyano, azido, optionally substituted hydrazino, —$COOR^{10}$, —$CONR^{11}R^{12}$ (wherein $R^{10-12}$ are each hydrogen, alkyl, phenyl or aralkyl); and n is 0 or 1; with the proviso that when $R^5$ and $R^6$ are of the formula (a), X is =C($R^7$)— and either one of Ra, Rb, $R^7$ and $R^8$ is —NRcRd, —NReRf, azido, optionally substituted hydrazino, —$COOR^{10}$ or —$CONR^{11}R^{12}$, or Ra and Rb together form an optionally hydrogenated 5- or 6-membered aromatic ring which may have, in the ring, at least one of nitrogen atom, sulfur atom and oxygen atom;

isomers thereof and pharmaceutically acceptable acid addition salts thereof, (4) pharmaceutical compositions containing, as an active ingredient, a 4-amino(alkyl)cyclohexane-1-carboxamide compound of the above (1)–(3), an isomer thereof or a pharmaceutically acceptable acid addition salt thereof, (5) antihypertensive agents containing, as an active ingredient, a 4-amino(alkyl)cyclohexane-1-carboxamide compound of the above (1)–(3), an isomer thereof or a pharmaceutically acceptable acid addition salt thereof, (6) therapeutic agents for angina pectoris, containing, as an active ingredient, a 4-amino(alkyl)cyclohexane-1-carboxamide compound of the above (1)–(3), an isomer thereof or a pharmaceutically acceptable acid addition salt thereof (7) therapeutic agents for asthma, containing, as an active ingredient, a 4-amino(alkyl)cyclohexane-1-carboxamide compound of the above (1)–(3), an isomer thereof or a pharmaceutically acceptable acid addition salt thereof, and (8) agents for improving peripheral circulation, containing, as an active ingredient, a 4-amino(alkyl)cyclohexane-1-carboxamide compound of the above (1)–(3), an isomer thereof or a pharmaceutically acceptable acid addition salt thereof.

Of the compounds of the aforementioned (1) and (2), preferred are:
trans-N-(1H-pyrrolo[2,3-b]pyridin-4-yl)-4-aminomethylcyclohexanecarboxamide,
trans-N-(1H-pyrazolo[3,4-b]pyridin-4-yl)-4-aminomethylcyclohexanecarboxamide,
(+)-trans-N-(1H-pyrrolo[2,3-b]pyridin-4-yl)-4-(1-aminoethyl)cyclohexanecarboxamide.
trans-N-(1H-pyrrolo[2,3-b]pyridin-4-yl)-4-(1-amino-1-methylethyl)cyclohexanecarboxamide,
(+)-trans-N-(1H-pyrazolo[3,4-b]pyridin-4-yl)-4-(1-aminoethyl)cyclohexanecarboxamide,
trans-N-(1H-pyrazolo[3,4-b]pyridin-4-yl)-4-(1-amino-1-methylethyl)cyclohexanecarboxamide,
trans-N-(2-methanesulfonylamino-4-pyridyl)-4-aminomethylcyclohexanecarboxamide,
(+)-trans-N-(2,3-dihydro-1H-pyrrolo[2,3-b]pyridin-4-yl)-4-(1-aminoethyl)cyclohexanecarboxamide,
(+)-trans-N-(2,3-dihydro-2-oxo-1H-pyrrolo[2,3-b]pyridin-4-yl)-4-(1-aminoethyl)cyclohexanecarboxamide,
(+)-trans-N-(2-methylcarbamoyl-4-pyridyl)-4-(1-aminoethyl)cyclohexanecarboxamide,
(+)-trans-N-(2-(2,2-dimethylhydrazino)-4-pyridyl)-4-(1-aminoethyl)cyclohexanecarboxamide,
(+)-trans-N-(2-methylamino-4-pyridyl)-4-(1-aminoethyl)cyclohexanecarboxamide,
(+)-trans-N-(2-ethylamino-4-pyridyl)-4-(1-aminoethyl)cyclohexanecarboxamide, isomers thereof and pharmaceutically acceptable acid addition salts thereof;

of the compounds of the aforementioned (1) and (3), preferred are:
trans-N-(1H-pyrrolo[2,3-b]pyridin-4-yl)-4-guanidinomethylcyclohexanecarboxamide,
trans-N-(1H-pyrazolo[3,4-b]pyridin-4-yl)-4-guanidinomethylcyclohexanecarboxamide,
trans-N-(1H-pyrrolo[2,3-b]pyridin-4-yl)-4-(2-imidazolin-2-yl)aminomethylcyclohexanecarboxamide,
trans-N-(1H-pyrrolo[2,3-b]pyridin-4-yl)-4-(1-methylguanidinomethyl)cyclohexanecarboxamide,
N'-[trans-(4-(1H-pyrrolo[2,3-b]pyridin-4-yl)carbamoyl)cyclohexylmethyl]formamidine,
trans-N-(2,3-dihydro-2-oxo-1H-pyrrolo[2,3-b]pyridin-4-yl)-4-guanidinomethylcyclohexanecarboxamide,
trans-N-(2,3-dihydro-1H-pyrrolo[2,3-b]pyridin-4-yl)-4-guanidinomethylcyclohexanecarboxamide, isomers thereof and pharmaceutically acceptable acid addition salts thereof.

With regard to each symbol in the formula (I), halogen means chlorine, bromine, fluorine or iodine; alkyl means straight- or branched chain alkyl having 1 to 10, preferably 1 to 6 carbon atoms, which is exemplified by methyl, ethyl, propyl, isopropyl, butyl, isobutyl, sec-butyl, tert-butyl, pentyl, isopentyl, neopentyl, hexyl, heptyl, 2-ethylhexyl, octyl, nonyl or decyl; haloalkyl means the aforementioned alkyl substituted by 1 to 5 halogens, which is exemplified by trifluoromethyl, 2,2,2-trifluoroethyl or 2,2,3,3,3-pentafluoropropyl; alkoxy means straight- or branched chain alkoxy having 1 to 6 carbon atoms, which is exemplified by methoxy, ethoxy, propoxy, isopropoxy, butoxy, isobutoxy, sec-butoxy, tert-butoxy, pentyloxy, isopentyloxy, neopentyloxy or hexyloxy; cycloalkyl means that having 3 to 7 carbon atoms, which is exemplified by cyclopropyl, cyclobutyl, cyclopentyl, cyclohexyl or cycloheptyl; cycloalkylalkyl means that wherein the cycloalkyl moiety is the aforementioned cycloalkyl having 3 to 7 carbon atoms and the alkyl moiety is straight- or branched chain alkyl having 1 to 6 carbon atoms (e.g. methyl, ethyl, propyl, isopropyl, butyl, pentyl, hexyl) and is exemplified by cyclopropylmethyl, cyclobutylmethyl, cyclopentylmethyl, cyclohexylmethyl, cycloheptylmethyl, cyclopropylethyl, cyclopentylethyl, cyclohexylethyl, cycloheptylethyl, cyclopropylpropyl, cyclopentylpropyl, cyclohexylpropyl, cycloheptylpropyl, cyclopropylbutyl, cyclopentylbutyl, cyclohexylbutyl, cycloheptylbutyl, cyclopropylhexyl, cyclopentylhexyl, cyclohexylhexyl or cyloheptylhexyl; alkylene means straight- or branched chain alkylene having 1 to 6 carbon atoms, which is exemplified by methylene, ethylene, trimethylene, tetramethylene, pentamethylene, hexamethylene, methylmethylene, dimethylmethylene, ethylmethylene, diethylmethylene, propylmethylene, propylene, methyltrimethylene, dimethylethylene, dimethyltrimethylene or dimethyltetramethylene; aralkyl means that wherein the alkyl moiety is alkyl having 1 to 4 carbon atoms and is exemplified by phenylalkyl such as benzyl, 1-phenylethyl, 2-phenylethyl, 3-phenylpropyl and 4-phenylbutyl; alkylidene means straight- or branched chain alkylidene having 1 to 6 carbon atoms, which is exemplified by methylidene, ethylidene, propylidene, isopropylidene, butylidene, pentylidene or hexylidene; phenylalkylidene means that wherein the alkylidene moiety is alkylidene having 1 to 6 carbon atoms, and is exemplified by benzylidene, phenylethylidene, phenylpropylidene, phenylbutylidene, phenylpentylidene or phenylhexylidene.

Examples of the substituents for cycloalkyl having 3 to 7 carbon atoms, and cycloalkylalkyl, phenyl, aralkyl, piperidyl and pyrrolidinyl, which may have substituent, include halogen, alkyl, alkoxy, aralkyl, haloalkyl, nitro, —NRcRd (wherein Rc and Rd may be the same or different and each is hydrogen, alkyl, —COR$^9$, —COOR$^{9'}$, —SO$_2$R$^{9''}$ or Rc and Rd, together with the nitrogen atom binding therewith, form a heterocyclic ring which may have, in the ring, oxygen atom, sulfur atom or optionally substituted nitrogen atom), cyano, azido, formyl, acyl, —COOR$^{10}$, —CONR$^{11}$R$^{12}$ or optionally substituted hydrazino. As used herein, halogen, alkyl, alkoxy, aralkyl and haloalkyl are as defined above and acyl is exemplified by acetyl, propionyl, butyryl, valeryl, pivaloyl, benzoyl, phenylacetyl, phenylpropionyl or phenylbutyryl.

Examples of the substituent for the optionally substituted hydrazino include alkyl, aralkyl, nitro and cyano, wherein alkyl and aralkyl are as defined above.

The heterocyclic ring optionally having, in the ring, oxygen atom, sulfur atom or optionally substituted nitrogen atom, which is formed by R$^x$ and R$^2$, Rc and Rd or Re and Rf, together with the nitrogen atom bonding therewith, is preferably a 5- or 6-membered ring or a bonded ring thereof and is exemplified by pyrrolidinyl, piperidyl, piperazinyl, morpholino and thiomorpholino. Examples of the substituent for the optionally substituted nitrogen atom include alkyl, aralkyl and haloalkyl, wherein alkyl, aralkyl and haloalkyl are as defined above.

The heterocyclic ring optionally having, in the ring, oxygen atom, sulfur atom or optionally substituted nitrogen atom, which is combinedly formed by R$^0$ and R, is exemplified by imidazol-2-yl, thiazol-2-yl, oxazol-2-yl, imidazolin-2-yl, 3,4,5,6-tetrahydropyridin-2-yl, 3,4,5,6-tetrahydropyrimidin-2-yl, 1,3-oxazolin-2-yl, 1,3-thiazolin-2-yl, and benzimidazol-2-yl, benzothiazol-2-yl, benzoxazol-2-yl and indol-2-yl which may have substituent such as halogen, alkyl, alkoxy, haloalkyl, nitro, amino, phenyl or aralkyl, wherein halogen, alkyl, alkoxy, haloalkyl and aralkyl are as defined above.

Examples of the substituent for the optionally substituted nitrogen atom include alkyl, aralkyl and haloalkyl, wherein alkyl, aralkyl and haloalkyl are as defined above.

When R$^5$ and R$^6$ are of the formula (a), (c), (e) or (f) and form a single ring, the ring is pyridine, pyrimidine, pyridazine, triazine, pyrazole or triazole. When the aforementioned R$^5$ and R$^6$ are of the formula (a), (b) or (d) and form a condensed ring, the ring is pyrrolopyridine (e.g. 1H-pyrrolo[2,3-b]pyridine, 1H-pyrrolo[3,2-b]pyridine, 1H-pyrrolo[3,4-b]pyridine), pyrazolopyridine (e.g. 1H-pyrazolo[3,4-b]pyridine, 1H-pyrazolo[4,3-b]pyridine), imidazopyridine (e.g. 1H-imidazo[4,5-b]pyridine), pyrrolopyrimidine (e.g. 1H-pyrrolo[2,3-d]pyrimidine, 1H-pyrrolo[3,2-d]pyrimidine, 1H-pyrrolo[3,4-d]pyrimidine), pyrazolopyrimidine (e.g. 1H-pyrazolo[3,4-d]pyrimidine, pyrazolo[1,5-a]pyrimidine, 1H-pyrazolo[4,3-d]pyrimidine), imidazopyrimidine (e.g. imidazo[1,2-a]pyrimidine, 1H-imidazo[4,5-d]pyrimidine), pyrrolotriazine (e.g. pyrrolo[1,2-a]-1,3,5-triazine, pyrrolo[2,1-f]-1,2,4-triazine), pyrazolotriazine (e.g. pyrazolo[1,5-a]-1,3,5-triazine), triazolopyridine (e.g. 1H-1,2,3-triazolo[4,5-b]pyridine), triazolopyrimidine (e.g. 1,2,4-triazolo[1,5-a]pyrimidine, 1,2,4-triazolo[4,3-a]pyrimidine, 1H-1,2,3-triazolo[4,5-d]pyrimidine), cinnoline, quinazoline, quinoline, pyridopyridazine (e.g. pyrido[2,3-c]pyridazine), pyridopyrazine (e.g. pyrido[2,3-b]pyrazine), pyridopyrimidine (e.g. pyrido[2,3-d]pyrimidine, pyrido[3,2-d]pyrimidine), pyrimidopyrimidine (e.g. pyrimido[4,5-d]pyrimidine, pyrimido[5,4-d]pyrimidine), pyrazinopyrimidine (e.g. pyrazino[2,3-d]pyrimidine), naphthyridine (e.g. 1,8-naphthyridine), tetrazolopyrimidine (e.g. tetrazolo[1,5-a]pyrimidine), thienopyridine (e.g. thieno[2,3-b]pyridine), thienopyrimidine (e.g. thieno[2,3-d]pyrimidine), thiazolopyridine (e.g. thiazolo[4,5-b]pyridine, thiazolo[5,4-b]pyridine), thiazolopyrimidine (e.g. thiazolo[4,5-d]pyrimidine, thiazolo[5,4-d]pyrimidine), oxazolopyridine (e.g. oxazolo[4,5-b]pyridine, oxazolo[5,4-b]pyridine), oxazolopyrimidine (e.g. oxazolo[4,5-d]pyrimidine, oxazolo[5,4-d]pyrimidine), furopyridine (e.g. furo[2,3-b]pyridine, furo[8,2-b]pyridine), furopyrimidine (e.g. furo[2,3-d]pyrimidine, furo[3,2-d]pyrimidine), 2,3-dihydropyrrolopyridine (e.g. 2,3-dihydro-1H-pyrrolo[2,3-b]pyridine, 2,3-dihydro-1H-pyrrolo[3,2-b]pyridine), 2,3-dihydropyrrolopyrimidine (e.g. 2,3-dihydro-1H-pyrrolo[2,3-d]pyrimidine, 2,3-dihydro-1H-pyrrolo[3,2-d]pyrimidine), 5,6,7,8-tetrahydropyrido[2,3-d]pyrimidine, 5,6,7,8-tetrahydro-1,8-naphthyridine or 5,6,7,8-tetrahydroquinoline. When these rings form hydrogenated aromatic rings, the carbon atom in the ring may be carbonyl and, for example, 2,3-dihydro-2-oxopyrrolopyridine, 2,3-dihydro-2,3-dioxopyrrolopyridine, 7,8-dihydro-7-oxonaphthyridine and 5,6,7,8-tetrahydro-7-oxonaphthyridine are included. These rings may be substituted by substituent such as halogen, alkyl, alkoxy, aralkyl, haloalkyl, nitro, —NRcRd, cyano, formyl, acyl, aminoalkyl, mono- or dialkylaminoalkyl, azido, —COOR$^{10}$, —CONR$^{11}$R$^{12}$ or optionally substituted hydrazino.

In the present invention, pharmaceutically acceptable acid addition salts of Compound (I) with inorganic acid or organic acid, hydrates and various solvates are encompassed. When the compound has a carboxyl group, metal salts such as sodium salt, potassium salt, calcium salt or aluminum salt and salts with amino acid, such as lysine and ornithine are also encompassed.

The present invention also encompasses cis- or transgeometrical isomers of Compound (I) and mixtures thereof. When the compound has an asymmetric carbon, the present invention also encompasses optical isomers and their racemates.

The Compound (I) of the present invention can be synthesized by the following methods.

Method 1

A method which comprises reacting a carboxylic acid compound of the formula

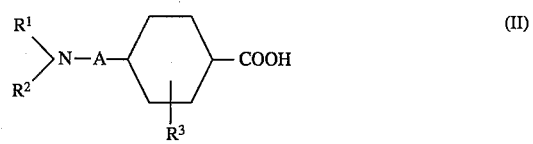

wherein each symbol is as defined above, or a reactive derivative thereof with an amino compound of the formula:

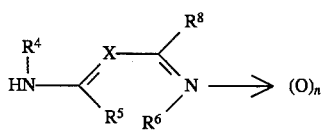

(III)

wherein each symbol is as defined above.

The reactive derivative of the carboxylic acid compound includes acid halides such as acid chloride, acid anhydrides, mixed acid anhydrides formed with, for example, ethyl chloroformate, esters such as methyl ester and ethyl ester and reactive derivatives formed with carbodiimide such as dicyclohexylcarbodiimide.

The reaction is carried out in the presence of an inert solvent, which is usually an organic solvent without a hydroxyl group, such as tetrahydrofuran, ethyl acetate, benzene, toluene, carbon tetrachloride, chloroform, methylene chloride, dimethylformamide or dimethylimidazolidinone. The reaction is carried out at an optional temperature, such as at −10°–200° C., preferably at 0°–80° C. When a reactive derivative which is not very reactive, such as an ester, is used as a starting material, the reaction is carried out at a high reaction temperature and when a highly reactive derivative, such as a mixed acid anhydride, is used, the reaction is carried out at a low reaction temperature.

Where necessary, an organic base such as pyridine, triethylamine or diisopropylethylamine is used as an acid scavenger. Also, the amino group of the compound of the formula (II) may be protected with an amino-protecting group such as benzyloxycarbonyl or t-butoxycarbonyl before reaction. Said protecting group may be eliminated by a conventional method after the reaction.

The carboxylic acid compound which is the starting compound for the synthesis in the present invention can be synthesized by the method described in Chem. Pharm. Bull., vol. 27, p. 2735 (1979) or ibid, vol. 27, p. 3039 (1979). In particular, when the carboxylic acid compound of the formula (II) is other than transamin (tranexamic acid), the compound can be synthesized by the following method.

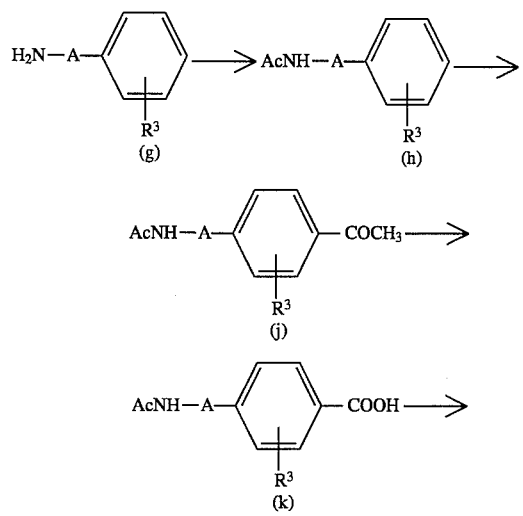

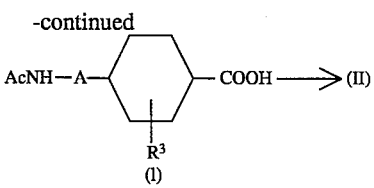

wherein Ac is an amino-protecting group such as acetyl and other symbols are as defined above.

That is, the amine compound of the formula (g) is protected with an amino-protecting group such as acetyl; an acetyl group is introduced onto an aromatic ring by Friedel-Crafts reaction; and a carboxylic acid compound of the formula (k) is obtained by a haloform reaction. Then, the aromatic ring is reduced by catalytic reduction and deprotected by an alkali hydrolysis to give a carboxylic acid compound of the formula (II) wherein $R^1$ and $R^2$ are hydrogen.

The cis- or trans-compound of the carboxylic acid compound of the formula (II) can be obtained, for example, as follows. A carboxylic acid compound of the formula (k) is subjected to a conventional column chromatography and recrystallized to give a cis-compound of the carboxylic acid compound of the formula (k). The carboxylic acid compound of the formula (k) is esterified by a conventional method and isomerized by the use of a base (e.g. sodium methoxide, potassium butoxide) to give a trans-compound of the carboxylic acid compound of the formula (k). Then, each isomer is deprotected by the method mentioned above.

An amine compound of the formula (III) which is the other synthetic starting compound can be synthesized by the method described in J. Med. Chem., vol. 25, p. 1258 (1982), ibid., vol. 32, p. 945 (1989), J. Heterocycl. Chem., vol. 20, p. 295 (1983), ibid. vol. 9, p. 235 (1972), ibid., vol. 1, p. 42 (1964), J. Am. Chem. Soc., vol. 77, p. 2256 (1955) and Zhurnal Organicheskoi Khimii, vol. 9, p. 1266 (1973).

In particular, a compound of the formula (II) wherein $R^1$ is

can be easily synthesized by the following synthetic method.

That is, a compound of the formula (IV)

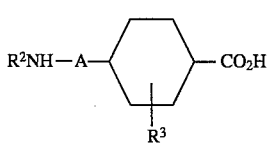

(IV)

wherein each symbol is as defined above, is condensed with a compound of the formula (V)

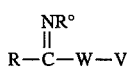

(V)

wherein R and $R^0$ mean the aforementioned groups or a protecting group such as t-butoxycarbonyl, benzyloxycarbonyl, acetyl or benzoyl, W means oxygen or sulfur and V means lower alkyl such as methyl, ethyl or propyl, benzyl, p-nitrobenzyl or 2-thienyl), or an acid addition salt thereof to give a desired compound.

Examples of the compound of the formula (V) include S-methylisothiourea, O-methylisourea, S-ethylisothiourea, O-ethylisourea, N,N'-S-trimethylisothiourea, N,N'-O-trimethylisourea, N,S-dimethylisothiourea, N,O-dimethylisourea, N-ethyl-S-methylisothiourea, N-ethyl-O-methylisourea, 2-methylthio-2-benzimidazole, 2-methylthio-2-benzothiazole, 2-methylthio-2-benzoxazole, 2-methylthio-2-imidazoline, 2-methoxy-2-imidazoline, 2-methylthio-3,4,5,6-tetrahydropyrimidine, 2-methylthiothiazoline, N,N'-dibenzyloxycarbonyl-S-methylisothiourea, N,N'-diacetyl-S-methylisothiourea, ethylformimidate, methylformimidate, methylacetoimidate, ethylacetoimidate, ethyl N-methylformimidate and methyl N-methylformimidate, and examples of their acid addition salts include hydroiodide, hydrobromide, hydrochloride, sulfate and p-toluenesulfonate.

The reaction generally proceeds in a preferable solvent such as water, alcohol alone (e.g. methanol, ethanol), a mixture of these with water, a polar solvent (e.g. dimethylformamide, dioxane, tetrahydrofuran), or a mixture of these with water. The compound of the formula (V) is preferably used in an amount of 1–10 fold moles and the reaction is preferably carried out at an optional temperature such as 0°–100° C. Where necessary, an inorganic base such as potassium carbonate, sodium carbonate, potassium hydroxide or sodium hydroxide or an organic base such as pyridine, 4-dimethylaminopyridine, triethylamine or diisopropylethylamine is preferably used as an acid scavenger.

Method 2

Of the compounds of the formula (I), a compound wherein one of $R^1$ and $R^2$ is hydrogen and the other is hydrogen or a group other than the formula (i) can be produced by reacting an amine compound of the formula (VI) wherein $R^1$ and $R^2$ are hydrogen, which is obtained by Method 1,

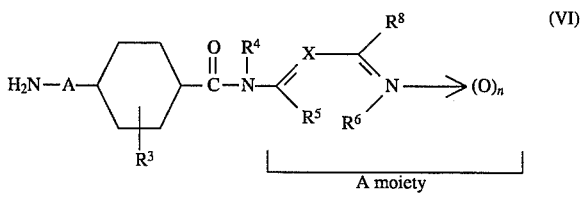

(VI)

wherein each symbol is as defined above, with a halide compound, an aldehyde compound or a ketone compound.

The halide compound to be used in this reaction is a compound of the formula (VII)

$R^{13}$—Hal (VII)

wherein $R^{13}$ is alkyl having 1 to 10 carbon atoms, or cycloalkyl having 3 to 7 carbon atoms, cycloalkylalkyl, phenyl, aralkyl, N-protected piperidyl or N-protected pyrrolidinyl, which may have substituent on the ring, and Hal is halogen which is preferably chlorine or bromine; the aldehyde compound is a compound of the formula (VIII)

$R^{14}$—CHO (VIII)

wherein $R^{14}$ is hydrogen, alkyl having 1 to 9 carbon atoms, or phenyl, aralkyl, N-protected piperidyl or N-protected pyrrolidinyl, optionally having substituent on the ring; and the ketone compound is a compound of the formula (IX)

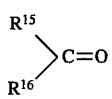

(IX)

wherein $R^{15}$ and $R^{16}$ are the same or different and each is alkyl having 1 to 9 carbon atoms, or phenyl, aralkyl, N-protected piperidyl or N-protected pyrrolidinyl, optionally having substituent on the ring, or $R^{15}$ and $R^{16}$ may, together with carbonyl group, form an optionally substituted cycloalkyl having 3 to 7 carbon atoms.

When the compound (VI) and a halide compound are reacted, the reaction can be carried out under the same conditions as in Method 1. It is preferable that deacidification condensation should be carried out in the presence of a base such as sodium carbonate, sodium hydrogencarbonate, sodium hydroxide, potassium hydroxide, triethylamine or pyridine.

When the compound (VI) and an aldehyde or a ketone are reacted, dehydrative condensation is generally carried out in a solvent hardly miscible with water, such as benzene, toluene, xylene, carbon tetrachloride, chloroform or dichloromethane while refluxing under heating. A small amount of an acid such as p-toluenesulfonic acid may be advantageously added.

Reduction of alkylidene, phenylalkylidene, pyrrolidilidene and piperidilidene obtained by the aforementioned condensation affords alkyl, aralkyl, pyrrolidinyl and piperidyl compounds.

The reduction can be carried out in an alcohol such as methanol, ethanol or isopropyl alcohol at −10°–100° C., preferably 0°–40° C. The reducing agent include, for example, sodium borohydride or sodium cyanoborohydride to be used in the presence of a small amount of an acid such as hydrochloric acid, hydrobromic acid or acetic acid. Further, the reduction is carried out by a catalytic reduction using Raney nickel, palladium-carbon or platinum oxide when the use thereof does not exert influence on other groups of the desired compound.

Method 3

Of the compounds of the formula (I), a compound wherein $R^1$ and $R^2$ form, together with the nitrogen atom binding therewith, a heterocyclic ring which may have, in the ring, oxygen atom, sulfur atom or optionally substituted nitrogen atom can be produced by reacting a compound of the formula (X)

(X)

or a compound of the formula (XI)

(XI)

with a compound of the formula (VI).

In the formulas (X) and (XI), $R^{17-24}$ are the same or different and each is hydrogen, halogen, alkyl having 1 to 6 carbon atoms, alkoxy having 1 to 6 carbon atoms, aralkyl, haloalkyl, nitro, amino, cyano or optionally substituted hydrazino, Y is carbon, oxygen, sulfur or optionally substituted nitrogen, and Z is a reactive group derived from an alcohol, such as halogen (e.g. chlorine, bromine) or sulfonyloxy (e.g. methanesulfonyloxy, p-toluenesulfonyloxy, trifluoromethanesulfonyloxy). The number of the substituent for the heterocyclic ring formed is 1 to 3.

The reaction proceeds under the same conditions as in Method 2.

Method 4

In the present invention, a compound wherein $R^1$ in the formula is $$-C\begin{matrix}NR°\\R\end{matrix}$$

can be also obtained by subjecting an amine compound of the formula $$R^2NH-A-\underset{R^3}{\underset{|}{\bigcirc}}-\overset{O}{\underset{||}{C}}-\underset{R^5}{\underset{|}{N}}-\overset{X}{\underset{R^6}{C}}=\underset{\diagup}{\overset{R^8}{C}}\underset{N}{\longrightarrow}(O)_n \quad (XII)$$

wherein each symbol is as defined above (which can be synthesized by the method described in Japanese Patent Application No. 255689/1991) and a compound of the formula (V) to condensation reaction.

The reaction proceeds under the same conditions as those for the reaction of the compounds (IV) and (V) in Method 1.

A compound (I) wherein $R^1$ is $$-C\begin{matrix}NR^0\\R\end{matrix}$$

and R is —NR'R" can be synthesized by Method 5 or Method 6 to be mentioned below.

Method 5

A compound (I) wherein $R^1$ is $$-C\begin{matrix}NR^0\\R\end{matrix}$$

and R is —NR'R" can be synthesized as follows. A compound of the formula (XII) is reacted with an iso(thio)cyanate compound of the formula (XIII)

$$R^0NC=X \qquad (XIII)$$

wherein each symbol is as defined above to give a (thio)ureido compound of the formula (XIV)

$$R^0NH-\overset{X}{\underset{||}{C}}-\underset{R^2}{\underset{|}{N}}-A-\underset{R^3}{\underset{|}{\bigcirc}}-\overset{O}{\underset{||}{C}}-\underset{R^5}{\underset{|}{N}}-\overset{X}{\underset{R^6}{C}}=\underset{\diagup}{\overset{R^8}{C}}\underset{N}{\longrightarrow}(O)_n \quad (XIV)$$

wherein each symbol is as defined above. The obtained compound is reacted with a suitable alkylating agent of the formula (XV)

$$(R^{25})_m-X^1 \qquad (XV)$$

wherein $R^{25}$ is alkyl or aralkyl, $X^1$ is halogen (e.g. chlorine, bromine, iodine) or sulfonyloxy (e.g. methanesulfonyloxy, p-toluenesulfonyloxy, trifluoromethanesulfonyloxy) and m is 1 or 2, to give a compound of the formula (XVI)

$$R^0N=\underset{R^2}{\underset{|}{C}}-\underset{R^3}{\underset{|}{N}}-A-\underset{}{\bigcirc}-\overset{O}{\underset{||}{C}}-\underset{R^5}{\underset{|}{N}}-\overset{X}{\underset{R^6}{C}}=\underset{\diagup}{\overset{R^8}{C}}\underset{N}{\longrightarrow}(O)_n \quad (XVII)$$

wherein each symbol is as defined above, and the obtained compound is reacted with an amine derivative of the formula (XVII)

$$R'R''NH \qquad (XVII)$$

wherein each symbol is as defined above to give a desired compound.

Examples of isocyanate or isothiocyanate compound of the formula (XIII) include methyl isocyanate, methyl isothiocyanate, ethyl isocyanate, ethyl isothiocyanate, phenyl isocyanate and phenyl isothiocyanate. When $R^1$ is hydrogen, sodium isocyanate, sodium isothiocyanate and ammonium thiocyanate are particularly used.

Examples of a suitable alkylating agent of the formula (XV) include methyl iodide, ethyl iodide, benzyl bromide, p-nitrobenzyl bromide, 2-thienyl bromide, dimethyl sulfate and diethyl sulfate.

The amine derivative of the formula (XVII) may be, for example, ammonia, methylamine, ethylamine, propylamine, aniline, benzylamine, phenethylamine or N-methyl-N-benzylamine.

The reaction of the compounds (XII) and (XIII) is carried out in an alcohol solvent such as methanol or ethanol, or in a solvent such as tetrahydrofuran, acetonitrile, dimethylformamide, chloroform or methylene chloride. The reaction temperature is 0°–200° C., particularly preferably from room temperature to 100° C. The reaction for some compounds can be promoted by the addition of an organic base such as pyridine and triethylamine. When $R^1$ is hydrogen, the reaction is carried out in an acidic aqueous solution such as hydrochloric acid or sulfuric acid.

The reaction of the compounds (XIV) and (XV) is carried out in a solvent such as acetone, tetrahydrofuran, acetonitrile, chloroform, dimethylformamide or dimethylimidazolidinone. The reaction temperature is from 0° C. to 150° C., particularly preferably from room temperature to 100° C.

Where necessary, a base such as sodium hydride, potassium carbonate or sodium methoxide may be used.

The reaction of the compounds (XVI) and (XVII) is carried out without or in a solvent, such as an alcohol solvent (e.g. methanol, ethanol) or polar solvent (e.g. tetrahydrofuran, acetonitrile, dimethylformamide). An amine derivative of the formula (XVII) is preferably used in an amount of 0.5–1.5 equivalents relative to the compound (XVI) and when reaction is not affected thereby, it may be used in an amount of 1.5–10 equivalents. The reaction temperature is from −20° C. to 150° C., preferably from 0° C. to 100° C. This reaction can be promoted by the addition of a base or a metal salt in an amount of 0.01–10 equivalents, preferably 0.1–3 equivalents. Examples of the base include inorganic base such as potassium carbonate, sodium carbonate or sodium hydrogencarbonate and organic base such as pyridine, triethylamine and 4-dimethylaminopyridine. The organic base may be used as a solvent. As the metal salt, usable are copper chloride, copper bromide, copper acetate, copper sulfate or mercury acetate.

A compound of the formula (I) wherein $R^1$ is

and R is —NR'R" can be obtained by directly reacting a compound (XIV) and a compound (XVII) in accordance with the reaction of the aforementioned compounds (XIII) and (XIV).

Method 6

A compound of the formula (I) wherein $R^1$ is

and R is —NR'R" can be synthesized by reacting a compound of the formula (XII) with a cyano compound of the formula (XVIII)

$$X^2—CN \quad (XVIII)$$

wherein $X^2$ is halogen such as chlorine or bromine to give a cyanamide compound of the formula (XIX)

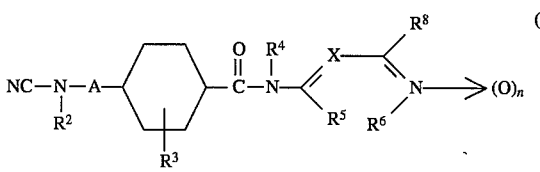

wherein each symbol is as defined above and the obtained cyanamide compound is reacted with an amine derivative of the formula (XVII).

The reaction of the compounds (XII) and (XVIII) is carried out in a solvent such as tetrahydrofuran, ether, acetone, methanol, ethanol, acetonitrile, dimethylformamide, dimethylimidazolidinone, chloroform or dichloromethane. The reaction temperature is from −20° C. to 150° C., particularly preferably 0°–80° C. In the instant reaction, an inorganic base such as potassium acetate, sodium acetate, potassium carbonate or sodium carbonate or an organic base such as pyridine, triethylamine or 4-dimethylaminopyridine is used.

The reaction of the compounds (XIX) and (XVII) is carried out without or in an alcohol solvent such as methanol or ethanol, or a polar solvent such as acetone, tetrahydrofuran, dioxane or dimethylformamide. The amine derivative of the formula (XVII) is preferably used in an amount of 0.8–1.5 equivalents relative to the cyanamide compound (XIX). The derivative may be used in an amount of 1.5–10 equivalents when the use thereof does not affect the reaction. The reaction can be promoted by the addition of a base in an amount of 0.01–10 equivalents, preferably 0.1–3 equivalents. Examples of the base include organic bases such as pyridine, triethylamine and 4-dimethylaminopyridine and inorganic bases such as sodium carbonate, potassium carbonate, sodium hydroxide, potassium hydroxide and sodium hydrogencarbonate.

Method 7

A compound of the formula (I) wherein $R^1$ and $R^2$ are the same or different and each is alkyl, phenyl, aralkyl or a group of the formula

wherein R and $R^0$ combinedly form a heterocyclic ring which may have, in the ring, oxygen atom, sulfur atom or optionally substituted nitrogen atom, or $R^1$ and $R^2$ form, together with the nitrogen atom binding therewith, a heterocyclic ring which may have, in the ring, oxygen atom, sulfur atom or optionally substituted nitrogen atom, can be produced by reacting a compound of the formula (VI) wherein the substituent for the heterocyclic ring in the A moiety is other than —NRcRd, —NReRf and hydrazino, and sodium nitrite or potassium nitrite in the presence of hydrochloric acid, sulfuric acid, formic acid or acetic acid to convert the compound to a hydroxyl compound of the formula (XX)

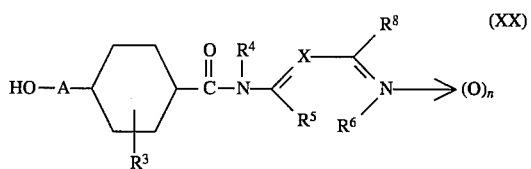

wherein each symbol is as defined above, and the hydroxyl compound is reacted with a halogenating agent such as thionyl chloride, phosphorous oxychloride, phosphorous trichloride, phosphorus pentachloride or phosphorus tribromide, or with methanesulfonyl chloride or p-toluenesulfonyl chloride in the presence of an acid scavenger to give a corresponding reactive derivative of the alcohol. Then, the derivative is reacted with an amine compound of the formula (XXI)

wherein $R^{1'}$ and $R^{2'}$ are the same or different and each is alkyl, phenyl, aralkyl, or

wherein R and $R^0$ combinedly form a heterocyclic ring which may have, in the ring, oxygen atom, sulfur atom or optionally substituted nitrogen atom, or $R^1$ and $R^2$ form, together with the nitrogen atom binding therewith, a heterocyclic ring which may have, in the ring, oxygen atom, sulfur atom or optionally substituted nitrogen atom.

The reaction is carried out in the presence of a suitable base such as inorganic base such as hydroxide, carbonate or hydrogencarbonate of alkali metal and alkaline earth metal (e.g. sodium hydroxide, potassium carbonate, sodium hydrogencarbonate) or organic base (e.g. pyridine, triethylamine).

The isomers to be encompassed by the Compound (I) of the present invention are produced by isolation from mixtures of the isomers by conventional methods or by the use of the starting material for each isomer.

In the Compound (I) of the present invention thus obtained, the amino group of the 4-position substituted amino moiety in the cyclohexane ring, the amino group when Ra, Rb, $R^7$ and $R^8$ are —NRcRd or —NReRf, and the amino group when $R^5$ and $R^6$ form a single ring or a condensed ring and the substituent in or on the ring is —NRcRd may be protected by the conventional aminoprotecting group such as alkanoyl having 1 to 5 carbon atoms (e.g. formyl, acetyl, propionyl, butyryl, isobutyryl, pivaloyl, valeryl); alkoxycarbonyl having 2 to 5 carbon atoms (e.g. methoxycarbonyl, ethoxycarbonyl, propoxycarbonyl, isopropoxycarbonyl, butoxycarbonyl, isobutoxycarbonyl, tert-butoxycarbonyl); cycloalkylcarbonyl having 4 to 8 carbon atoms such as cyclopropylcarbonyl, cyclobutylcarbonyl, cyclopentylcarbonyl, cyclohexylcarbonyl, cycloheptylcarbonyl); aroyl (e.g. benzoyl, naphthoyl) [as used herein, aroyl means those optionally substituted by, for example, halogen, alkyl having 1 to 6 carbon atoms, alkoxy having 1 to 6 carbon atoms, aralkyl, trifluoromethyl, nitro or amino]; phenylalkoxycarbonyl (e.g. benzyloxycarbonyl, phenylethoxycarbonyl, phenylpropoxycarbonyl, phenylbutoxycarbonyl) [as used herein, phenylethoxycarbonyl means those optionally having, on the phenyl ring, substituent such as halogen, alkyl having 1 to 6 carbon atoms, alkoxy having 1 to 6 carbon atoms, aralkyl, trifluoromethyl, nitro or amino]; phenylalkenyl (e.g. styryl, cinnamyl, phenylbutenyl, phenylpentenyl, phenylhexenyl); phenylalkylidene (e.g. benzylidene, phenylethylidene); a group forming pyrrolidylidene, piperidilydene or phthalimido; alkylcarbamoyl (e.g. methylcarbamoyl, ethylcarbamoyl, dimethylcarbamoyl, diethylcarbamoyl, dipropylcarbamoyl); alkylcarbamoylalkyl (e.g. methylcarbamoylmethyl, ethylcarbamoylmethyl, dimethylcarbamoylmethyl, diethylcarbamoylmethyl, dimethylcarbamoylethyl); alkoxymethyl (e.g. methoxymethyl, ethoxymethyl, propoxymethyl, butoxymethyl, tert-butoxymethyl); aralkyloxyalkyl (e.g. benzyloxymethyl, p-methoxybenzyloxymethyl, o-nitrobenzyloxymethyl); allyl; or cyclic ether (e.g. tetrahydrofuran, tetrahydropyran).

The above-mentioned amino-protecting group can be removed by treating with conventional acids such as hydrochloric acid, sulfuric acid, formic acid, acetic acid, trifluoroacetic acid, hydrobromic acid/acetic acid, hydrochloric acid/dioxane, hydrogen fluoride, methanesulfonic acid and trifluoromethane-sulfonic acid, Lewis acids such as boron trifluoride-ether complex, titanium tetrachloride, tin tetrachloride, aluminum chloride, boron tribromide and trimethylsilyl iodide, or alkali such as ammonia, sodium methoxide, sodium ethoxide, sodium carbonate, potassium carbonate, sodium hydrogencarbonate, potassium hydrogencarbonate, sodium hydroxide, potassium hydroxide or hydrazine.

Deprotection can be also carried out by catalytic reduction using 5% palladium carbon, 10% palladium carbon, 10% palladium hydroxide carbon, Raney nickel as a catalyst, reduction using metal sodium or metal lithium in liquid ammonia, or reduction using sodium borohydride, lithium aluminum hydride, diborane, zinc or sodium amalgam as a reducing agent. Furthermore, a method using an oxidizing agent such as hydrogen peroxide, potassium permanganate, 2,3-dichloro-5,6-dicyano-1,4-benzoquinone (DDQ) or N-bromosuccinimide may be used.

The Compound (I) thus obtained can be separated and purified from reaction mixtures by a method known per se such as recrystallization and chromatography.

Moreover, the compounds of the formula (I) can be converted to pharmaceutically acceptable acid addition salts thereof according to a conventional manner. The acid for forming pharmaceutically acceptable acid addition salts can be suitably selected from inorganic acids (e.g. hydrochloric acid, hydrobromic acid, sulfuric acid, phosphoric acid) and organic acids (e.g. acetic acid, methanesulfonic acid, maleic acid, fumaric acid). These salts can be converted to the corresponding free base according to a conventional manner, for example, by reacting with an alkali such as sodium hydroxide or potassium hydroxide. The compound of the formula (I) can be also converted to a quaternary ammonium salt thereof. Of the compounds of the formula (I), the compounds having a carboxyl group can be converted to salts with metal (e.g. sodium, potassium, calcium, aluminum) or amino acid (e.g. lysine, ornithine).

The action of the compounds of the present invention is explained in detail by way of pharmacological experiments.

Pharmacological Experiment 1

Catheters for blood pressure measurement and for drug administration were previously inserted into carotid artery and jugular vein of spontaneously hypertensive rats (SHR) weighing 350–450 g. Effects of 0.3 mg/kg of each test compound intravenously administered on the blood pressure were observed in the conscious, unrestrained SHR. The blood pressure was automatically measured and analyzed with a pressure transducer.

The results are given in Table 1.

TABLE 1

| Compound | Dose (mg/kg) | Antihypertensive action (mmHg) (SHR i.v.) |
|---|---|---|
| Example 3 | 0.3 | −62 |
| Example 4 | 0.3 | −77 |
| Example 6 | 0.3 | −96 |
| Example 7 | 0.3 | −53 |

Pharmacological Experiment 2

Male rabbits (weighing 1.9–3.0 kg) were anesthetized with sodium pentobarbital and dehematized to remove thoracic aorta. Ring strips (about 2 mm wide) were prepared and suspended in a 40 ml-Magnus bath filled with Krebs-Henseleit solution (NaCl 117 mM; KCl 4.7 mH; $CaCl_2$ 2.5 mH; $MgSO_4$ 1.2 mM; $NaHCO_3$ 24.8 mM; $KH_2PO_4$ 1.2 mM; glucose 11.0 mM). The resting tension of 2 g was applied. The Magnus bath was constantly aerated with a mixed gas (95% oxygen+5% carbon dioxide gas). The tension of the strips was measured by an isometric transducer (TB-611T, Nihon Kohden, Japan). The strips were contracted with phenylephrine ($10^{-6}$M) and after the contraction became stable, the compounds were cumulatively added to the bath and relaxing response was observed. The vasodilating action of the compounds was expressed as $IC_{50}$ (μM), the concentration required to inhibit phenylephurine-induced contraction (which was taken as 100%) by half. The results are shown in Table 2.

TABLE 2

| Compound | Vasodilation (μM) |
| --- | --- |
| Example 3 | 0.09 |
| Example 4 | 0.08 |
| Example 6 | 0.12 |
| Example 7 | 0.19 |

Pharmacological Experiment 3: Effect on coronary blood flow

Groups of 2 or 3 adult mongrel dogs were anesthetized with an intravenous administration of 30 mg/kg body weight of sodium pentobarbital. According to the method of Yago et al [Folia Pharmacologica Japonica, vol. 57, p. 380 (1961)], the left coronary artery was perfused and its blood flow was measured. Test compound was injected into the coronary artery at a volume of 10–300 μg. The effects of the test compound on coronary blood flow were expressed as $ED_{50}$ (μg), the dose required to increase the coronary blood flow by a half of the effects by the coronary artery injection of 3 μg of nifedipine [dimethyl 2,6-dimethyl-4-(2-nitrophenyl)-1,4-dihydropyridine-3,5-dicarboxylate]. The results are summarized in Table 3.

The half life (T ½, minute) was also measured as the duration of effects.

TABLE 3

| Test compound | Increase in coronary blood flow ($ED_{50}$, μg) (T ½; min.) |
| --- | --- |
| Example 3 | 8.8 (2.7) |
| Example 4 | 7.0 (3.8) |
| Example 6 | 4.3 (3.0) |
| Example 7 | 20 (6.7) |

Pharmacological Experiment 4: Effect on acetylcholine-induced contraction of trachea specimen isolated from guinea pigs Male Hartley guinea pigs weighing 260–390 g were anesthetized with sodium pentobarbital (100 mg/kg, i.p.). The guinea pigs were then dehematized and trachea was isolated. Ventral cartilage of the trachea was incised and ligament was insected to give 3 mm wide strips. The strips were suspended in a 40 ml-Magnus bath filled with Krebs-Henseleit solution (NaCl 117 mM; KCl 4.7 mM; $CaCl_2$ 2.5 mM; $MgSO_4$ 1.2 mM; $NaHCO_3$ 24.8 mM; $KH_2PO_4$ 1.2 mM; glucose 11.0 mM). The resting tension of 1 g was applied. The Magnus bath was constantly aerated with a mixed gas (95% oxygen+5% carbon dioxide gas). The tension of the strips was measured with an isometric transducer (TB-611T, Nihon Kohden, Japan) and recorded on a recorder (Ti-102, Tokai Irika, Japan). The strips were contracted with acetylcholine ($10^{-6}$M) and after the contraction became stable, the compounds were cumulatively added to the bath and relaxing response was observed. The relaxation by the compounds was expressed as $IC_{50}$ (μM), the concentration required to inhibit the papaverine ($10^{-4}$M)-induced response (which was taken as 100%) by half. The results are shown in Table 4.

TABLE 4

| Compound | Bronchodilation ($IC_{50}$; μM |
| --- | --- |
| Example 3 | 0.06 |
| Example 4 | 0.09 |

TABLE 4-continued

| Compound | Bronchodilation ($IC_{50}$; μM |
| --- | --- |
| Example 6 | 0.17 |
| Example 7 | 0.31 |

Pharmacological Experiment 5: Effects on experimental asthma caused by histamine inhalation in guinea pig According to Suyama [Allergy, vol. 15, p. 549 (1966)], female Hartley guinea pigs weighing 490–630 g were placed in an aerosol inhalation device, and 0.2% histamine solution (histamine chloride, Nakarai Kagaku, Japan) was sprayed with an ultrasonic nebulizer (TUR-3200, Nihon Kohden, Japan). Protective action was examined using collapsing as an index. Inhalation of the test compound was performed by placing the guinea pigs in the aforementioned aerosol inhalation device and spraying the test compound dissolved in a physiological saline to a predetermined concentration for 5 minutes. Then, the guinea pigs were allowed to immediately inhale histamine and delay in collapsing by dyspnea was measured. The results are shown in Table 5.

TABLE 5

| Compound | Concentration (%) | Average time until collapsing (second) |
| --- | --- | --- |
| Example 3 | 0.01 | 152.4 ± 12.2 |
| | 0.1 | 235.4 ± 40.2 |

Acute toxicity test

Each of the compounds of Examples 3, 6, 86 and 87 was intraperitoneally administered to ddY mice. All mice survived for five days after intraperitoneal administration of 30 mg/kg.

The Compound (I), isomers thereof and pharmaceutically acceptable acid addition salts thereof of the present invention have coronary and cerebral blood flow increasing action as do calcium antagonists, and have additional renal and peripheral artery blood flow increasing action which conventional calcium antagonists do not have. The blood flow increasing action lasts over a long period of time and antihypertensive action is very strong. In addition, they are effective for not only blood vessel contraction induced by biological substances such as endothelin but also for blood vessel contraction induced by calcium ionophore or phorbol ester on which calcium antagonists fail to show action.

Accordingly, the compounds of the present invention are useful as a potent and long-lasting antihypertensive agent and an agent for the prevention and treatment of diseases in circulatory organs such as coronary, cerebral, renal and peripheral arteries.

Moreover, the compounds of the present invention exhibit inhibitory action on experimental asthma caused by histamine inhalation in guinea pigs and inhibitory action on acetylcholine-induced contraction of trachea strips isolated from guinea pigs, and thus are useful as therapeutic agents for asthma.

When the compounds (I) of the present invention are used as medicines, an effective amount thereof is usually admixed with pharmacologically acceptable additives such as excipients, carriers and diluents and orally or parenterally administered in the form of tablet, granule, powder, capsule, injection, ointment or suppository.

While the dosage varies depending on age, body weight, symptom and so on of patients, a daily dose for a human adult is generally in the range of from about 5 to 500 mg for oral administration at single dose or several times divided doses.

While the present invention is explained in more detail by the following examples, these examples are not to be construed as limiting the present invention.

EXAMPLE 1

(a) To a mixture of 4,6-diaminopyrimidine (4.7 g), ethanol (500 ml) and water (200 ml) was added 1N sodium hydroxide (13.25 ml) while cooling with ice water. After the dropwise addition of 1N hydrochloric acid (26.5 ml) thereto, benzyloxycarbonyl chloride (4.5 g) was dropwise added thereto. After being stirred at room temperature for 2 hours, the mixture was concentrated under reduced pressure to give crystals. The crystals were collected by filtration and recrystallized from chloroform:methanol=5:1 to give 2.4 g of N-benzyloxycarbonyl-4,6-diaminopyrimidine, melting point 194° C.

(b) A solution (20 ml) of trans-4-benzyloxycarboxamidomethyl cyclohexanecarbonyl chloride (2.6 g) in 1,3-dimethyl-2-imidazolidinone was dropwise added to a mixture of N-benzyloxycarbonyl- 4,6-diaminopyrimidine (1.7 g), triethylamine (2.9 ml) and 1,3-dimethyl-2-imidazolidinone (40 ml) with stirring while cooling with ice water, and the mixture was stirred at room temperature for 1.5 hours. The reaction mixture was poured into water to give a precipitation of yellow, gum-like insoluble material. The precipitate was washed with cold water, dried, concentrated and added with ethyl acetate. The obtained crystals were collected by filtration to give 1.6 g of trans-N-(6-benzyloxycarboxamide-4-pyrimidyl)-4-benzyloxycarboxa midomethyl cyclohexanecarboxamide, melting point 187° C.

(c) A solution (50 ml) of the compound (800 mg) obtained in (b), conc. hydrochloric acid (0.5 ml) and 10% palladium carbon (400 mg) in methanol was aerated with hydrogen gas to carry out a catalytic reduction. The reaction proceeded at room temperature for 4 hours. The reaction mixture was filtered and the filtrate was concentrated under reduced pressure to give crystals. The crystals were collected by filtration and recrystallized from ethanol to give 150 mg of trans-N-(6-amino-4-pyrimidyl)-4-aminomethyl cyclohexanecarboxamide dihydrochloride ³⁄₂ hydrate, melting point 245°–247° C.

EXAMPLE 2

(a) A solution (20 ml) of trans-4-benzyloxycarboxamidomethyl cyclohexanecarbonyl chloride (1.86 g) in dichloromethane was dropwise added to a mixture of 4-amino-1H-pyrrolo[2,3-b]pyridine (400 mg), triethylamine (1.2 ml) and dichloromethane (50 ml) over 30 minutes with stirring while cooling with ice water, and the mixture was stirred at room temperature for 3 hours. The mixture was heated to 45°–50° C. and allowed to react for 3 hours.

After cooling, the reaction mixture was poured into water. The dichloromethane layer was washed with a sodium hydrogencarbonate solution. dried and concentrated. The residue was purified by silica gel column chromatography (chloroform:methanol=50:1) to give 970 mg of trans-N-(1H-pyrrolo[2,3-b]pyridin-4-yl)-4-benzyloxycarboxamidomethyl cyclohexanecarboxamide.

(b) The compound (33 mg) obtained in Example 2 (a) and 30% hydrogen bromide in acetic acid (5 ml) were stirred at room temperature for 30 minutes. The reaction mixture was concentrated under reduced pressure, added with ether and the crystals obtained were sufficiently washed with ether. The crystals were recrystallized from ethanol to give 24 mg of trans-N-(1H-pyrrolo[2,3-b]pyridin-4-yl)-4-aminomethyl cyclohexanecarboxamide dihydrobromide, melting point 262° C. (decomposition).

EXAMPLE 3

(a) Acetic anhydride (38.4 g) was dropwise added to a solution (200 ml) of (R)-(+)-1-phenylethylamine (30 g) in chloroform under ice-cooling. After completion of the reaction, ice water was added thereto and the mixture was extracted with chloroform. The extract was washed with 1N aqueous solution of sodium hydroxide and water. After drying, the mixture was concentrated under reduced pressure to give crystals, which were recrystallized from isopropyl ether to give 32.2 g of (+)-N-( 1-phenylethyl)acetamide. $[\alpha]_D=+143.5°$ (ethanol, c=1)

PMR(CDCl$_3$/TMS) δ: 1.48(3H,d,J=6 Hz), 1.98(3H, s), 5.12(1H,m), 5.75(1H, brs), 7.31(5H, s)

Aluminum chloride (185 g) was portionwise added to a solution (300 ml) of the obtained (+)-N-(1-phenylethyl)acetamide (103 g) and acetyl chloride in dichloroethane. After stirring at the same temperature for 1 hour, the mixture was further stirred at 50°–60° C. for 3 hours. After completion of the reaction, the reaction mixture was poured into ice water and extracted with chloroform. The extract was washed with water, dried and concentrated under reduced pressure. The crystals obtained were recrystallized from ethanol-isopropyl ether to give 62.8 g of (+)-N-(1-(4-acethylphenyl)ethyl)acetamide. $[\alpha]_D=+162.0°$ (methanol, c=1)

PMR(CDCl$_3$/TMS) δ: 1.46(3H, d,6 Hz), 2.01(3H, s), 2.58(3H, s), 5.13(1H,m), 6.20(1H,brs), 7.38(2H,d,J=8 Hz), 7.90(2H, d,J=8 Hz)

After 10% sodium hypochlorite (760 ml) was dropwise added to a solution (540 ml) of (+)-N-(1-(4-acethylphenyl)ethyl)acetamide (61.4 g) and sodium hydroxide (12.6 g) in methanol, the mixture was stirred at 50°–70° C. for 1 hour. After completion of the reaction, the solvent was distilled away under reduced pressure and the residue obtained was poured into ice water. Addition of conc. hydrochloric acid to make the mixture acidic resulted in precipitation of crystals. The crystals were collected by filtration under reduced pressure, washed with water and dried to give 51.2 g of (+)-4-(1-acetamidoethyl)benzoic acid. $[\alpha]_D+136.8°$ (methanol, c=1)

PMR(CD$_3$OD/TMS) δ: 1.43(3H,d,J=7 Hz), 1.96(3H, s), 5.00(1H,m), 7.40(2H, d,J=8 Hz), 7.95(2H,d,J=8 Hz)

A solution (220 ml) of (+)-4-(1-acetamidoethyl)benzoic acid (51.2 g) and 5% ruthenium carbon (35.4 g) in 28% aqueous ammonia was stirred in an autoclave at initial hydrogen pressure of 70 atm and at 90° C. for 3 hours and then at 150° C. for 3 hours. After completion of the reaction, the catalyst was filtered off and the filtrate was concentrated under reduced pressure to give 53.5 g of a cis- and transmixture of (+)-4-(1-acetamidoethyl)cyclohexanecarboxylic acid. Then, a solution of 31% hydrochloric acid-methanol (33 ml) and methanol (200 ml) were added thereto and the mixture was refluxed for 4 hours. After completion of the reaction, the mixture was concentrated under reduced pressure and the residue obtained was poured into ice water and extracted with chloroform. The extract was washed with water, dried and concentrated under reduced pressure. The residue obtained was purified by silica gel column chromatography to give 38.0 g of a cis- and transmixture (2:1) of methyl (+)-4-(1-acetamidoethyl)cyclohexanecarboxylate. $[\alpha]_D=+11.4°$ (methanol, c=1)

Potassium tert-butoxide (37.7 g) was added to a solution (200 ml) of a cis- and trans- mixture of methyl (+)-4-(1-acetamidoethyl)cyclohexanecarboxylate (38.0 g) in methanol and the mixture was refluxed under heating for 60 hours. After completion of the reaction, the mixture was concentrated under reduced pressure and the residue obtained was poured into ice water, neutralized with conc. hydrochloric acid and extracted with chloroform. The extract was washed with water, dried and concentrated under reduced pressure to give 21 g of methyl (+)-trans-4-(1-acetamidoethyl)cyclohexanecarboxylate. $[\alpha]_D=+41.6°$ (methanol, c=1)

PMR(CDCl$_3$/TMS) δ: 0.90–2.30(10H,m), 1.09(3H, d,J=7 Hz), 1.98 (3H, s), 3.66(3H, s), 5.74(1H,m)

Water (10 ml) and potassium hydroxide (66 g) were added to a solution (250 ml) of methyl (+)-trans-4-(1-acetamidoethyl)cyclohexanecarboxylate (63 g) in methanol and the mixture was refluxed under heating for 50 hours. After completion of the reaction, the reaction mixture was concentrated under reduced pressure. The residue obtained was poured into ice water and neutralized with dilute sulfuric acid. The precipitate was filtered off under reduced pressure and 4N aqueous solution of sodium hydroxide (41.8 ml) was added to the filtrate containing (+)-trans-4-(1-aminoethyl)cyclohexanecarboxylic acid under ice cooling. Then, benzyloxycarbonyl chloride (28.5 g) and 4N sodium hydroxide (41.8 ml) were dropwise added thereto alternatively at said temperature. After completion of the reaction, conc. hydrochloric acid was added to the reaction mixture to make same acidic, which resulted in precipitation of crystals. The crystals were collected by filtration under reduced pressure and dried to give 25.9 g of (+)-trans-4-(1-benzyloxycarboxamidoethyl)cyclohexanecarboxylic acid, melting point 125°–126° C. $[\alpha]_D=+7.5°$ (ethanol, c=1)

PMR(CDCl$_3$/TMS) δ: 0.90–2.30(10H,m), 1.10(3H,7 Hz), 4.58(1H, brs), 5.09(2H, s), 7.35(5H, s)

(b) Thionyl chloride (5 ml) and a drop of dimethylformamide were added to a solution (60 ml) of (+)-trans-4-(1-benzyloxycarboxamidoethyl)cyclohexanecarboxylic acid (6 g) in dichloromethane and the mixture was refluxed under heating for 1 hour. After completion of the reaction, the solvent was distilled away under reduced pressure to give crystals of (+)-trans- 4-(1-benzyloxycarboxamidoethyl)cyclohexanecarbonyl chloride. The crystals were dissolved in acetonitrile (40 ml) and the solution was dropwise added to a solution (50 ml) of 4 -amino-1H-pyrrolo[2,3-b]pyridine (1 g) and diisopropylethylamine (4.7 ml) in acetonitrile. The mixture was stirred at room temperature for 5 hours. The precipitated crystals were collected by filtration, dried and dissolved in dimethylformamide (200 ml ) and methanol (100 ml ). Thereto was added sodium methoxide (460 mg) and the mixture was stirred at 40° C. for 10 minutes. After completion of the reaction, the reaction mixture was concentrated under reduced pressure and to the resultant residue was added water to give crystals. The crystals were collected by filtration, washed with ethyl acetate and recrystallized from chloroform-methanol to give 2.6 g of (+)-trans-N-(1H-pyrrolo[2,3-b]pyridin-4-yl)-4-(1-benzyloxycarboxamidoethyl)cyclohexanecarboxamide.

PMR(DMSO-d$_6$/TMS) δ: 0.80–2.10(10H, m), 1.04(3H, d,J=6 Hz), 3.20(1H, m), 5.01(2H, s), 6.80(1H, d,J=3 Hz), 7.35(6H, s), 7.80(1H, d, J=5 Hz), 8.06(1H,d,J=5 Hz), 9.80(1H, s)

A solution (70 ml) of (+)-trans-N-(1H-pyrrolo[2,3-b] -pyridin-4-yl)-4-(1-benzyloxycarboxamidoethyl)cyclohexanecarboxamide (2.6 g), 10% palladium hydroxide carbon (500 mg) and 15% hydrochloric acid-methanol (4 ml) in methanol was stirred in an autoclave at initial hydrogen pressure of 5 atm and at room temperature for 1 hour.

After completion of the reaction, the catalyst was filtered off and the filtrate was concentrated under reduced pressure to give crystals which were then recrystallized from ethanol to give 1.15 g of (+)-trans-N-(1H-pyrrolo[2,3-b]pyridin-4-yl)-4-(1-aminoethyl)cyclohexanecarboxamide dihydrochloride, melting point 220°–223° C. $[\alpha]_D=+3.32°$ (methanol, c=0.5)

PMR(DM SO-d$_6$/TMS) δ: 0.70–2.20(10H,m), 1.14(3H,d, J=6 Hz), 3.05(1H, m), 7.23(1H,d,J=3 Hz), 7.55(1H,d,J=3 Hz), 8.29(1H, d,J=6 Hz), 8.31(1H,d,J=6 Hz)

EXAMPLE 4

(a) Acetyl chloride (62 g) was dropwise added to a solution (1 l) of cumylamine (90 g) and a 48% aqueous solution of sodium hydroxide (70 ml) in toluene under ice-cooling and the mixture was stirred at room temperature for 5 hours. After completion of the reaction, the mixture was neutralized with a saturated aqueous solution of potassium carbonate and extracted with ethyl acetate. The extract was washed with water and dried. The solvent was distilled away under reduced pressure to give 102.3 g of N-(1-methyl-1-phenylethyl)acetamide.

PMR(CDCl$_3$/TMS) δ: 1.70(6H,s), 1.96(3H, s), 5.70(1H, brs), 7.20–7.50(5H,m)

Aluminum chloride (41.5 g) was portionwise added to a solution (75 ml) of N-(1-methyl-1-phenylethyl)acetamide (25 g) and acetyl chloride (16.6 g) in dichloroethane under ice-cooling. The mixture was stirred at said temperature for 1 hour and then at 50°–60° C. for 1 hour. After completion of the reaction, the reaction mixture was poured into ice water and extracted with chloroform. The extract was washed with water, dried and concentrated under reduced pressure to give crystals which were then recrystallized from ethyl acetate-isopropyl ether to give 20.4 g of N-(1-(4-acetylphenyl)-1-methylethyl)acetamide.

PMR(CDCl$_3$/TMS) δ: 1.69(6H, s), 1.98(3H, s), 2.56(3H, s), 5.82 (1H,brs), 7.46(2H,d,J=9 Hz), 7.95(2H, d,J=9 Hz)

After 10% sodium hypochlorite (240 ml) was dropwise added to a solution (250 ml) of N-(1-(4-acethylphenyl)-1-methylethyl)acetamide (20.4 g) and sodium hydroxide (3.9 g) in methanol, the mixture was stirred at 50°–70° C. for 1 hour. After completion of the reaction, the solvent was distilled away under reduced pressure and the residue obtained was poured into ice water. Addition of conc. hydrochloric acid to make the mixture acidic resulted in precipitation of crystals. The crystals were collected by filtration under reduced pressure, washed with water and dried to give 17.9 g of 4-(1-acetamido-1-methylethyl)benzoic acid.

PMR(CDCl$_3$/TMS) δ: 1.67(6H, s), 1.96(3H, s), 7.42(2H, d,J=9 Hz), 7.88(2H,d,J=9 Hz), 8.11(1H, s), 12.50(1H,m)

A solution (200 ml) of 4-(1-acetamido-1-methylethyl)benzoic acid (17.9 g) and 5% ruthenium carbon (60 g) in 10% aqueous ammonia was stirred in an autoclave at initial hydrogen pressure of 70 atm and at 150°–170° C. for 3 hours. After completion of the reaction, the catalyst was filtered off and the filtrate was concentrated under reduced pressure to give a cis- and trans- mixture of 4-(1-acetamido-1-methylethyl)cyclohexanecarboxylic acid. Then, 31% hydrochloric acid-methanol (15 ml ) and methanol (100 ml ) were added thereto and the mixture was refluxed for 4 hours. After completion of the reaction, the mixture was concentrated under reduced pressure and the residue was extracted with chloroform. The extract was washed with water, dried and concentrated under reduced pressure. The residue obtained was purified by silica gel column chromatography to give 14.0 g of a cis- and trans-mixture (3:1) of methyl 4-(1-acetamido-1-methylethyl)cyclohexanecarboxylate.

Potassium tert-butoxide (30.0 g) was added to a solution (150 ml) of a cis- and trans- mixture of methyl 4-(1-acetamido-1-methylethyl)cyclohexanecarboxylate (30.8 g) in methanol and the mixture was refluxed under heating for 40 hours. After completion of the reaction, the residue obtained by concentration under reduced pressure was poured into ice water, neutralized with conc. hydrochloric acid and extracted with chloroform. The extract was washed with water, dried and concentrated under reduced pressure. The resultant crystals were recrystallized from methanol to give 24.5 g of methyl trans-4-(1-acetamido-1-methylethyl)cyclohexanecarboxylate.

PMR(CDCl$_3$/TMS) δ: 0.80–2.40(10H,m), 1.26(6H, s), 1.92(3H, s), 3.66(3H, s), 5.26(1H, brs)

A solution (100 ml) of methyl trans-4-(1-acetamido-1-methylethyl)cyclohexanecarboxylate (24.5 g) in 4N potassium hydroxide was refluxed under heating for 50 hours. After completion of the reaction, conc. hydrochloric acid (11.6 ml) was added thereto under ice-cooling and benzyloxycarbonyl chloride (20.8 g) was dropwise added thereto at said temperature. The mixture was stirred at room temperature for 5 hours. After completion of the reaction, conc. hydrochloric acid was added to the reaction mixture under ice-cooling to make same acidic, which resulted in precipitation of crystals. The crystals were collected by filtration under reduced pressure and dried to give 22.1 g of trans-4-(1-benzyloxycarboxamido-1-methylethyl)cyclohexanecarboxylic acid, melting point 83°–85° C.

PMR (CDCl$_3$/TMS) δ: 0.80–2.30 (10H, m), 1.26(6H,s), 4.66(1H, brs), 5.05(2H, s), 7.36(5H, s)

(b) Thionyl chloride (5.2 ml) and a drop of dimethylformamide were added to a solution (65 ml) of trans-4-(1-benzyloxycarboxamido-1-methylethyl)cyclohexanecarboxylic acid (6.2 g) in dichloromethane and the mixture was refluxed under heating for 1 hour. After completion of the reaction, the solvent was distilled away under reduced pressure to give crystals of trans-4-(1-benzyloxycarboxamido-1-methylethyl)cyclohexanecarbonyl chloride. The crystals were dissolved in acetonitrile (50 ml) and the solution was dropwise added to a solution (50 ml) of 4-amino-1H-pyrrolo[2,3-b]pyridine (1 g) and diisopropylethylamine (5.4 ml) in acetonitrile under ice-cooling and the mixture was stirred at room temperature for 5 hours. After completion of the reaction, water was added thereto and the mixture was extracted with ethyl acetate. The extract was washed with water, dried and concentrated under reduced pressure. The crystals thus obtained were dissolved in dimethylformamide (60 ml) and methanol (60 ml). Thereto was added sodium methoxide (281 mg) under ice-cooling and the mixture was stirred at room temperature for 1 hour. After completion of the reaction, to the residue obtained by concentration was added water and the mixture was extracted with ethyl acetate. The extract was washed with water, dried and concentrated. The resultant crystals were recrystallized from chloroform-methanol to give 1.6 g of trans-N-(1H-pyrrolo-[2,3-b]pyridin-4-yl)-4-(1-benzyloxycarboxamido-1-methylethyl)cyclohexanecarboxamide.

PMR(DMSO-d$_6$/TMS) δ: 0.80–2.10(10H,m), 1.16(6H, s), 4.99(2H, s), 6.80(1H, brs), 6.85(1H, d,J=3 Hz), 7.35(6H, s), 7.80(1H, d,J=6 Hz), 8.06(1H, d,J=6 Hz), 9.76(1H, s)

A solution (50 ml) of trans-N-(1H-pyrrolo[2,3-b]pyridin-4-yl)-4-(1-benzyloxycarboxamido-1-methylethyl)cyclohexanecarboxamide (1.6 g), 10% palladium hydroxide carbon (250 mg) and 15% hydrochloric acid-methanol (4 ml) in methanol was stirred in an autoclave at initial hydrogen pressure of 5 atm and at room temperature for 1 hour.

After completion of the reaction, the catalyst was filtered off and the filtrate was concentrated under reduced pressure to give crystals. Recrystallization of the crystals from ethanol-ethyl acetate gave 930 mg of trans-N-(1H-pyrrolo[2,3-b]pyridin-4-yl)-4-(1-amino-1-methylethyl)cyclohexanecarboxamide dihydrochloride monohydrate, melting point 288° C. (decomposition).

PMR(DMSO-d$_6$/TMS) δ: 0.80–2.20(10H,m), 1.21(6H,s), 7.30(1H, d, J=3 Hz), 7.59(1H, d, J=3 Hz), 8.07(2H, brs), 8.22(1H, d, J=6 Hz), 8.30 (1 H, d, J =6 Hz), 10.91(1H,s), 12.68(1H, brs)

The corresponding dihydrobromide trihydrate, melting point 225°–228° C.

EXAMPLE 5

(a) Phosphorus oxychloride (60 ml) and phosphorus pentachloride (20 mg) were added to 1-benzyl-4-hydroxy-1H-pyrazolo[3,4-b] pyridine (13.8 g) and the mixture was refluxed under heating for 2 hours. After completion of the reaction, phosphorus oxychloride was distilled away under reduced pressure and the residue obtained was poured into ice water. The mixture was neutralized with 2N aqueous solution of sodium hydroxide and the resultant crystals were collected by filtration. After drying, the crystals were recrystallized from ethyl acetate-hexane to give 13.5 g of 1-benzyl-4-chloro-1H-pyrazolo[3,4-b]pyridine.

PMR(CDCl$_3$/TMS) δ: 5.71(2H, s), 7.12(1H, d,J=5 Hz), 7.31(5H, s), 8.11(1H, s), 8.42(1H,d,J=5 Hz)

Sodium azide (2.5 g) was added to a solution (50 ml) of 1-benzyl-4-chloro-1H-pyrazolo[3,4-b]pyridine (4.7 g) in dimethylformamide and the mixture was stirred at 100°–120° C. for 1 hour. After completion of the reaction, the reaction mixture was poured into ice water, made acidic with acetic acid and extracted with ethyl acetate. The extract was washed with water, dried and concentrated under reduced pressure. The residue obtained was purified by silica gel column chromatography to give 2.7 g of 4-azido-1-benzyl-1H-pyrazolo[3,4-b]pyridine.

PMR(CDCl$_3$/TMS) δ: 5.70(2H,s), 6.79(1H, d,J=5 Hz), 7.31(5H, s), 8.10(1H, s), 8.46(1H, d,J=5 Hz)

A solution (40 ml) of 4-azido-1-benzyl-1H-pyrazolo[3,4-b]pyridine (2.7 g), 10% palladium hydroxide carbon (1.0 g) and 15% hydrochloric acid-methanol (1 ml) in methanol was stirred in an autoclave at initial hydrogen pressure of 10 atm and at 40°–50° C. for 5 hours. After completion of the reaction, the catalyst was filtered off and the filtrate was concentrated under reduced pressure to give crystals. Recrystallization from methanol-ethyl acetate gave 1.9 g of 4-amino-1H-pyrazolo[3,4-b]pyridine dihydrochloride.

PMR(DMSO-d$_6$/TMS) δ: 3.16(2H,brs), 6.18(1H,d,J=5 Hz), 7.90(1H, d,J=5 Hz), 8.13(1H,s)

(b) A solution (5 ml) of trans-4-benzyloxycarboxamidomethyl cyclohexanecarbonyl chloride (485 mg) in dichloromethane was dropwise added to a solution (20 ml) of 4-amino-1H-pyrazolo[3,4-b]pyridine dihydrochloride (270 mg) and diisopropylethylamine (0.68 ml) in 1,3-dimethyl-2-imidazolidinone under ice-cooling and the mixture was stirred at room temperature for 5 hours. After completion of the reaction, the reaction mixture was concentrated under reduced pressure. Water was added to the obtained residue and the mixture was extracted with ethyl acetate. The extract was washed with water, dried and concentrated under reduced pressure. The residue obtained was purified by silica gel column chromatography to give 370 mg of trans-N-(1H- pyrazolo[3,4-b]pyridin-4-yl)-4-benzyloxycarboxamidomethyl cyclohexanecarboxamide.

PMR(DMSO-d$_6$/TMS) δ: 0.80–2.10(10H,m), 2.90(2H, m), 5.03(2H, s), 7.35(5H, s), 7.76(1H, d,J=5 Hz), 8.33(1H, d,J=5 Hz), 8.36(1H, s)

Trans-N-(1H-pyrazolo[3,4-b]pyridin-4-yl)-4-benzyloxycarboxamidomethyl cyclohexanecarboxamide (370 mg) and 25% hydrogen bromide in acetic acid (10 ml) were stirred at room temperature for 15 minutes. After completion of the reaction, the reaction mixture was concentrated under reduced pressure. The crystals obtained were washed with ether and recrystallized from methanol-ethyl acetate to give 330 mg of trans-N-(1H-pyrazolo[3,4-b]pyridin-4-yl)-4-aminomethylcyclohexanecarboxamide dihydrobromide ½ hydrate.

PMR(DMSO-d$_6$/TMS) δ: 0.90–2.22(10H,m), 3.05(2H, m), 8.00(4H, m), 8.51(1H,d,J=5 Hz), 8.93(1H, s), 11.31(1H, brs)

EXAMPLE 6

A solution (10 ml) of (+)-trans-4-(1-benzyloxycarboxamidoethyl)cyclohexanecarbonyl chloride (760 mg) in 1,3-dimethyl-2-imidazolidinone was dropwise added to a solution (50 ml) of 4-amino-1H-pyrazolo[3,4-b]pyridine dihydrochloride (390 mg) and diisopropylethylamine (1.8 ml) in 1,3-dimethyl-2-imidazolidinone under ice-cooling and the mixture was stirred at room temperature for 5 hours. After completion of the reaction, the reaction mixture was poured into water and extracted with ethyl acetate. The extract was washed with water, dried and concentrated under reduced pressure. The residue obtained was purified by silica gel column chromatography to give 550 mg of (+)-trans-N-(1H-pyrazolo[3,4-b]pyridin-4-yl)-4-(1-benzyloxycarboxamidoethyl)cyclohexanecarboxamide.

PMR(DMSO-d$_6$/TMS) δ: 0.80–2.15(13H, m), 5.03(2H, s), 7.01(1H, m), 7.37(5H, s), 7.78(1H,d,J=5t{z), 8.35(1H, d,J=5 Hz), 8.38(1H, s), 10.30(1H,s)

A solution (15 ml) of (+)-trans-N-(1H-pyrazolo[3,4-b]pyridin-4-yl)-4-(1-benzyloxycarboxanaidoethyl)cyclohexanecarboxamide (580 mg), 10% palladium hydroxide carbon (200 mg) and 15% hydrochloric acid-methanol (1 ml) in methanol was stirred in an autoclave at initial hydrogen pressure or 5 atm and at room temperature for 1 hour. After completion of the reaction, the catalyst was filtered off and the filtrate was concentrated under reduced pressure to give crystals. Recrystallization of the crystals from ethanol gave 310 mg of (+)-trans-N-(1H-pyrazolo[3,4-b]pyridin-4-yl)-4-(1-aminoethyl)cyclohexanecarboxamide dihydrochloride, melting point 294° C. (decomposition). [α]$_D$=+4.2° (methanol, c=0.5)

PMR(DMSO-d$_6$/TMS) δ: 0.90–2.25(13H,m), 3.10(1H, m), 7.99(4H,m), 8.52(1H, d,J=5 Hz), 8.93(1H, s), 11.20(1H, brs)

EXAMPLE 7

A solution (20 ml) of trans-4-(1-benzyloxycarboxamido-1-methylethyl)cyclohexanecarbonyl chloride (3.9 g) in acetonitrile was dropwise added to a solution (100 ml) of 4-amino-1H-pyrazolo[3,4-b]pyridine dihydrochloride (1.0 g) and diisopropylethylamine (4.6 ml) in acetonitrile under ice-cooling and the mixture was stirred at room temperature for 3 hours. After completion of the reaction, water was added to the reaction mixture and the mixture was extracted with ethyl acetate. The extract was washed with water, dried and concentrated under reduced pressure. The residue obtained was purified by silica gel column chromatography to give 630 mg of trans-N-(1H-pyrazolo[3,4-b]pyridin-4-yl)-4-(1-benzyloxycarboxamido-1-methylethyl)cyclohexanecarboxamide.

PMR(CDCl$_3$/TMS) δ: 0.80–2.60(10H, m), 1.26(6H, s), 5.05(2H, s), 7.33(5H, s), 7.82(1H,d,J=5 Hz), 8.14(1H, s), 8.40(1H, d,J=5 Hz)

A solution (60 ml) of trans-N-(1H-pyrazolo[3,4-b]pyridin-4-yl)-4-(1-benzyloxycarboxamido-1-methylethyl)cyclohexanecarboxamide (630 mg) and 10% palladium hydroxide carbon (300 mg) in methanol was stirred in an autoclave at initial hydrogen pressure of 5 atm and at room temperature for 1 hour. After completion of the reaction, the catalyst was filtered off and the filtrate was concentrated under reduced pressure to give crystals, to which was added 15% hydrochloric acid-methanol (5 ml). The mixture was concentrated again to give crystals which were recrystallized from methanol-ethyl acetate to give trans-N-(1H-pyrazolo[3,4-b]pyridin-4-yl)-4-(1-amino-1-methylethyl)cyclohexanecarboxamido dihydrochloride ½ hydrate, melting point 278°–279° C.

PMR(DMSO-d$_6$/TMS) δ: 0.80–2.30(10H, m), 1.23(6H, s), 7.98(4H, m), 8.50(1H,d,J=5 Hz), 8.85(1H,s), 11.09(1H, brs)

EXAMPLE 8

(a) Sodium azide (1.31 g) and ammonium chloride (1.07 g) were added to a solution of 4-amino-2-chloropyridine (2 g) in dimethylformamide (20 ml) and the mixture was stirred at 110° C. for 10 hours. After the insoluble material was filtered off, the filtrate was concentrated under reduced pressure. The residue obtained was purified by silica gel column chromatography to give 1.83 g of 4-amino-2-azidopyridine, melting point 220° C. (decomposition).

PMR(DMSO-d$_6$/TMS) δ: 6.55(2H, s), 6.67(1H,d,J=2 Hz), 6.76(1H, dd, J=2,8 Hz), 8.78(1H,d,J=8 Hz)

(b) Diisopropylethylamine (1 ml) was added to a solution of 4-amino-2-azidopyridine (0.41 g) in dimethylformamide (20 ml) and the mixture was stirred at 40° C. A solution (10 ml) of (R)-(+)-trans-4-(1-benzyloxycarboxamidoethyl)cyclohexanecarbonyl chloride (1.73 g) in dimethylformamide was dropwise added thereto and the mixture was stirred at 50° C. for 24 hours. Ethyl acetate was added to the reaction mixture and the mixture was washed with water, dried and concentrated. The residue was purified by silica gel column chromatography to give 0.52 g of (R)-(+)-trans-N-(2-azido-4-pyridyl)-4-(1-benzyloxycarboxamidoethyl)cyclohexanecarboxamide, melting point 184°–186° C. [α]$_D$=+18.20° (methanol, c=0.5)

PMR (DMSO-d$_6$/TMS) δ: 0.9–2.2 (10H, m), 1.0(3H,d, J=6 Hz), 3.40(1H, m), 5.0(2H, s), 7.32(6H,brs), 8.45(1H, s), 9.14(1H,d, J=8 Hz), 10.55(1H,brs)

(c) A solution (50 ml) of the compound (200 mg) obtained in (b), 15% hydrochloric acid-methanol (0.5 ml) and 10% palladium hydroxide carbon (100 mg) in methanol was stirred in an autoclave at initial hydrogen pressure of 10 atm and at room temperature for 5 hours. The reaction mixture was filtered and the filtrate was concentrated under reduced pressure to give crystals, which were recrystallized from ethyl acetate-methanol to give 50 mg of (R)-(+)-trans-N-(2-amino-4-pyridyl)-4-(1-aminoethyl)cyclohexanecarboxamide dihydrochloride monohydrate, melting point 225° C. (decomposition). [α]$_D$=+4.25° (methanol, c=0.5)

EXAMPLE 9

(a) A solution (5 ml) of trans-4-benzyloxycarboxamidomethyl cyclohexanecarbonyl 1 chloride (1.76 g) in dichloromethane was dropwise added to a solution of 4-amino-1H-pyrazolo[3,4-d]pyrimidine (700 mg) and triethylamine (1.08 ml) in 1,3-dimethyl-2-imidazolidinone (20 ml) under ice-cooling and the mixture was stirred at room temperature for 5 hours. After completion of the reaction, the reaction mixture was poured into water and extracted with chloroform. The extract was washed with a saturated aqueous solution of sodium hydrogencarbonate and water, dried and concentrated. The residue obtained was purified by silica gel column chromatography (chloroform:methanol=10:1) to give 530 mg of trans-N-(1H-pyrazolo[3,4-d]pyrimidin-4-yl)-4-benzyloxycarboxamidomethylcyclohexanecarboxamide.

PMR(CDCl$_3$/TMS) δ: 0.9–2.3(10H, m), 3.11(2H, m), 4.80(1H, m), 5.12(2H, s), 7.36(5H, s), 8.33(1H, s), 8.82(1H, s)

(b) A solution of 25% hydrogen bromide in acetic acid (10 ml) was added to the compound (530 mg) obtained in Example 9 (a) and the mixture was stirred at room temperature for 1 hour. After completion of the reaction, the solvent was distilled away under reduced pressure. The crystals obtained were washed with ether and recrystallized from ethanol-ether to give 200 mg of trans-N-(1H-pyrazolo[3,4-d]pyrimidin-4-yl)-4-aminomethylcyclohexanecarboxamide dihydrobromide ½ hydrate, melting point 230° C. (decomposition).

EXAMPLE 10

A solution (20 ml) of (+)-trans-4-(1-benzyloxycarboxamidoethyl)cyclohexanecarbonyl chloride (2.4 g) in 1,3-dimethyl-2-imidazolidinone was dropwise added to a solution (130 ml) of 4-amino-1H-pyrazolo[3,4-d]pyrimidine (2.0 g) and diisopropylethylamine (2.6 ml) in 1,3-dimethyl-2-imidazolidinone under ice-cooling and the mixture was stirred at room temperature for 3 hours. After completion of the reaction, the reaction mixture was poured into water and extracted with ethyl acetate. The extract was washed with water, dried and concentrated. The residue obtained was purified by silica gel column chromatography to give 3.0 g of (+)-trans-N-(1H-pyrazolo[3,4-d]Pyrimidin-4-yl)-4-(1-benzyloxycarboxamidoethyl)cyclohexanecarboxamide.

PMR(CDCl$_3$/TMS) δ: 0.90–2.20(10H, m), 1.15(3H,d,J=6 Hz), 5.10 (2H,s), 7.36(5H,s), 8.58(1H,s), 8.70(1H,s)

A solution (30 ml) of (+)-trans-N-(1H-pyrazolo[3,4-d]-pyrimidin-4-yl)-4-(1-benzyloxycarboxamidoethyl)cyclohexanecarboxamide (410 mg) and 10% palladium hydroxide carbon (200 mg) in methanol was stirred in an autoclave at initial hydrogen pressure of 5 atm and at room temperature for 1 hour. After completion of the reaction, the catalyst was filtered off and the filtrate was concentrated under reduced pressure to give crystals, which were dissolved in 15% hydrochloric acid-methanol (5 ml). The mixture was concentrated again to give crystals which were recrystallized from ethanol-ethyl acetate to give 230 mg of (+)-trans-N-(1H-pyrazolo[3,4-d]pyrimidin-4-yl)-4-(1-aminoethyl)cyclohexanecarboxamide dihydrochloride, melting point 210°–213° C. [α]$_D$=+4.84° (methanol, e=0.5)

PMR (DMSO-d$_6$/TMS) δ: 0.96–2.30(10H,m), 1.14(3H,d, J=6 Hz), 7.85(2H,m), 8.44(1H,s), 8.60(1H,s)

EXAMPLE 11

(a) A solution (5 ml) of trans-4-(1-benzyloxycarboxamido-1-methylethyl)cyclohexanecarbonyl chloride (500 mg) in dichloromethane was dropwise added to a solution of 4-amino-1H-pyrazolo[3,4-d]pyrimidine (200 mg) and triethylamine (0.29 ml) in 1,3-dimethyl-2-imidazolidinone (20 ml) under ice-cooling and the mixture was stirred at room temperature for 3 hours. After completion of the reaction, the reaction mixture was poured into water and extracted with chloroform. The extract was washed with a saturated aqueous solution of sodium hydrogencarbonate and water, dried and concentrated. The residue obtained was purified by silica gel column chromatography (chloroform:methanol= 10:1) to give 310 mg of trans-N-(1H-pyrazolo[3,4-d]pyrimidin-4-yl)-4-(1-benzyloxycarboxamido-1-methylethyl)cyclohexanecarboxamide.

PMR(CDCl$_3$/TMS) δ: 0.9–2.5(10H, m), 1.27(3H,s), 1.29(3H,s), 4.69(1H,brs), 5.06(2H,s), 7.35(5H,s), 8.61(1H, s), 8.77(1H,s)

(b) A solution of 25% hydrogen bromide in acetic acid (5 ml) was added to the compound (310 mg) obtained in Example 11 (a) under ice-cooling and the mixture was stirred at said temperature for 1 hour. After completion of the reaction, the solvent was distilled away under reduced pressure. The crystals obtained were washed with ether and recrystallized from ethanol-ethyl acetate to give 150 mg of trans-N-(1H-pyrazolo[3,4-d]pyrimidin-4-yl)-4-(1-amino-1-methylethyl)cyclohexanecarboxamide dihydrobromide, melting point 260° C. (decomposition).

The following compounds can be synthesized according to the methods of the aforementioned Examples 1–11.

(12) Trans-N-(4-pyrimidinyl)-4-aminomethylcyclohexanecarboxamide dihydrobromide ¼ hydrate, m.p. 235°–237° C.

(13) Trans-N-(3-amino-4-pyridyl)-4-aminomethylcyclohexanecarboxamide dihydrobromide ¼ hydrate, m.p. 266°–269° C.

(14) Trans-N-(7H-imidazo[4,5-d]pyrimidin-6-yl)-4-aminomethylcyclohexanecarboxamide dihydrobromide ½ hydrate, m.p. 214°–216° C.

(15) Trans-N-(3H-1,2,3-triazolo[4,5-d]pyrimidin-7-yl)-4-aminomethylcyclohexanecarboxamide ⅔ hydrobromide, m.p. 195°–197° C.

(16) Trans-N-(1-benzyl-1H-pyrazolo[3,4-b]pyridin-4-yl)-4-aminomethylcyclohexanecarboxamide dihydrobromide, m.p. 267°–268° C.

(17) Trans-N-(1H-5-pyrazolyl)-4-aminomethylcyclohexanecarboxamide dihydrobromide, m.p. 251°–252° C.

(18) Trans-N-(1H-pyrazolo[3,4-b]pyridin-4-yl)-4-aminomethylcyclohexanecarboxamide dihydrobromide ½ hydrate, m.p. 261°–262° C.

(19) Trans-N-(4-pyridazinyl)-4-aminomethylcyclohexanecarboxamide dihydrochloride ⅔ hydrate, m.p. 258° C.

(20) Trans-N-(7H-pyrrolo[2,3-d]pyrimidin-4-yl)-4-aminomethylcyclohexanecarboxamide

(21) Trans-N-(2-amino-4-pyridyl)-4-aminomethylcyclohexanecarboxamide dihydrochloride ⅔ hydrate, m.p. 260° C. (decomposition)

(22) Trans-N-(thieno[2,3-d]pyrimidin-4-yl)-4-aminomethylcyclohexanecarboxamide dihydrobromide ½ hydrate, m.p. 243°–245° C.

(23) Trans-N-(imidazo[1,2-a]pyrimidin-5-yl)-4-aminomethylcyclohexanecarboxamide

(24) Trans-N-(5-methyl-1,2,4-triazolo[1,5-a]pyrimidin-7-yl)-4-aminomethylcyclohexanecarboxamide dihydrobromide, m.p. 297° C. (decomposition)

(25) Trans-N-(5-methyltetrazolo[1,5-a]pyrimidin-7-yl)-4-aminomethylcyclohexanecarboxamide

(26) Trans-N-(3-cyano-5-methylpyrazolo[1,5-a]pyrimidin-7-yl)-4-aminomethylcyclohexanecarboxamide hydrobromide dihydrate, m.p. 245°–246° C.

(27) Trans-N-(pyrido[2,3-d]pyrimidin-4-yl)-4-aminomethylcyclohexanecarboxamide

(28) Trans-N-(4-pyridyl)-4-iminomethylaminocyclohexanecarboxamide

(29) Trans-N-(1H-pyrazolo[3,4-b]pyridin-4-yl)-4-(1-amino-1-methylethyl)cyclohexanecarboxamide dihydrobromide ½ hydrate, m.p. 269°–270° C.

(30) Trans-N-(2-(1-pyrrolidinyl)-4-pyridyl)-4-aminomethylcyclohexanecarboxamide dihydrobromide ½ hydrate, m.p. 149°–151° C.

(31) Trans-N-(2,6-diamino-4-pyrimidinyl)-4-aminomethylcyclohexanecarboxamide dihydrobromide, m.p. 288°–289° C.

(32) (+)-Trans-N-(7-methyl-1,8-naphthylidin-4-yl)-4-(1-aminoethyl)cyclohexanecarboxamide 3 hydrochloride monohydrate, m.p. 220° C. (decomposition), $[\alpha]_D$=+ 4.65° (methanol, c=0.5)

(33) Trans-N-(1-benzyloxymethylpyrrolo[2,3-b]pyridin-4-yl)-4-aminomethylcyclohexanecarboxamide monohydrate, m.p. 118°–120° C.

(34) (+)-Trans-N-(1-methylpyrrolo[2,3-b]pyridin-4-yl)-4-(1-aminoethyl)cyclohexanecarboxamide dihydrochloride, m.p. 220° C. (decomposition), $[\alpha]_D$=+3.20° (methanol, c=1.0)

(35) Trans-N-benzyl-N-(2-benzylamino-4-pyridyl)-4-(1-aminomethylethyl)cyclohexanecarboxamide dihydrochloride, m.p. 190°–194° C.

(36) Trans-N-(2-benzylamino-4-pyridyl)-4-(1-amino-1-methylethyl)cyclohexanecarboxamide

(37) Trans-N-(2-amino-4-pyridyl)-4-(1-amino-1-methylethyl)cyclohexanecarboxamide

(38) Trans-N-(2-benzoylamino-4-pyridyl)-4-aminomethylcyclohexanecarboxamide

(39) Trans-N-(2-azido-4-pyridyl)-4-aminomethylcyclohexanecarboxamide, m.p. 219° C. (decomposition)

(40) Trans-N-(2-acetylamino-4-pyridyl)-4-aminomethylcyclohexanecarboxamide

(41) Trans-N-(2-methanesulfonylamino-4-pyridyl)-4-aminomethylcyclohexanecarboxamide

(42) Trans-N-(2-methylamino-4-pyridyl)-4-aminomethylcyclohexanecarboxamide

(43) Trans-N-(2-dimethylamino-4-pyridyl)-4-aminomethylcyclohexanecarboxamide

(44) Trans-N-(2-ethylamino-4-pyridyl)-4-aminomethylcyclohexanecarboxamide

(45) Trans-N-(2,3-dihydro-1H-pyrrolo[2,3-b]pyridin-4-yl)-4-aminomethylcycohexanecarboxamide
PMR(DMSO-$d_6$/TMS) δ: 0.72–2.20(9H,m), 2.60–3.10(7H,m), 6.12 (1H, br.s), 6.90(1H,d,J=6 Hz), 7.56(1H,d,J=6 Hz), 9.50(1H,br.s)

(46) (+)-Trans-N-(2,3-dihydro-1H-pyrrolo[2,3-b]pyridin-4-yl)-4-(1-aminoethyl)cyclohexanecarboxamide

(47) Trans-N-(2,3-dihydro-1H-pyrrolo[2,3-b]pyridin-4-y)-4-(1-amino-1-methylethyl)cyclohexanecarboxamide

(48) Trans-N-(2,3-dihydro-2-oxo-1H-pyrrolo[2,3-b]pyridin-4-yl)-4-aminomethylcyclohexanecarboxamide

(49) (+)-Trans-N-(2,3-dihydro-2-oxo-1H-pyrrolo[2,3-b]pyridin-4-yl)-4-(1-aminoethyl)cyclohexanecarboxamide

(50) Trans-N-(2,3-dihydro-2-oxo-1H-pyrrolo[2,3-b]pyridin-4-yl)-4-(1-amino-1-methylethyl)cyclohexanecarboxamide

(51) Trans-N-(2,3-dihydro-2,3-dioxo-1H-pyrrolo[2,3-b]pyridin-4-yl)-4-aminomethylcyclohexanecarboxamide

(52) (+)-Trans-N-(2,3-dihydro-2,3-dioxo-1H-pyrrolo[2,3-b]pyridin-4-yl)-4-(1-aminoethyl)cyclohexanecarboxamide

(53) Trans-N-(2,3-dihydro-2,3-dioxo-1H-pyrrolo[2,3-b]pyridin-4-yl)-4-(1-amino-1-methylethyl)cyclohexanecarboxamide

(54) Trans-N-(2-carboxy-4-pyridyl)-4-aminomethylcyclohexanecarboxamide
PMR(CDCl$_3$/TMS) δ: 0.56–2.32(12H,m), 2.38–2.62(2H, m), 7.34 (1H,s), 7.95(1H,dd,J=1.8, 5.4 Hz), 8.06–8.28(2H, m), 8.59(1H,d, J=5.4 Hz)

(55) Trans-N-(2-carbamoyl-4-pyridyl)-4-aminomethylcyclohexanecarboxamide

(56) (+)-Trans-N-(2-carbamoyl-4-pyridyl)-4-(1-aminoethyl)cyclohexanecarboxamide

(57) Trans-N-(2-carbamoyl-4-pyridyl)-4-(1-amino-1-methylethyl)cyclohexanecarboxamide

(58) Trans-N-(2-methylcarbamoyl-4-pyridyl)-4-aminomethylcyclohexanecarboxamide

(59) (+)-Trans-N-(2-methylcarbamoyl-4-pyridyl)-4-(1-aminoethyl)cyclohexanecarboxamide

(60) Trans-N-(2-methylcarbamoyl-4-pyridyl)-4-(1-amino-1-methylethyl)cyclohexanecarboxamide

(61) Trans-N-(2-hydrazino-4-pyridyl)-4-aminomethylcyclohexanecarboxamide

(62) Trans-N-(2-(2,2-dimethylhydrazino)-4-pyridyl)-4-aminomethylcyclohexanecarboxamide

(63) (+)-Trans-N-(2-(2,2-dimethylhydrazino)-4-pyridyl)-4-aminomethylcyclohexanecarboxamide

(64) Trans-N-(2-(2,2-dimethylhydrazino)-4-pyridyl)-4-(1-amino-1-methylethyl)cyclohexanecarboxamide

(65) Trans-N-(3-dimethylaminomethyl-1H-pyrrolo[2,3-b]pyridin-4-yl)-4-aminomethylcyclohexanecarboxamide

(66) Trans-N-(3-methyl-1H-pyrrolo[2,3-b]pyridin-4-yl)-4-aminomethylcyclohexanecarboxamide

(67) Trans-N-(3-formyl-1H-pyrrolo[2,3-b]pyridin-4-yl)-4-aminomethylcyclohexanecarboxamide

(68) Trans-N-(3-carboxy-1H-pyrrolo[2,3-b]pyridin-4-yl)-4-aminomethylcyclohexanecarboxamide

(69) Trans-N-(3-methoxycarbonyl-1H-pyrrolo[2,3-b]pyridin-4-yl)-4-aminomethylcyclohexanecarboxamide

(70) Trans-N-(3-carbamoyl-1H-pyrrolo[2,3-b]pyridin-4-yl)-4-aminomethylcyclohexanecarboxamide

(71) Trans-N-(1-pivaloyloxymethyl-1H-pyrrolo[2,3-b]pyridin-4-yl)-4-aminomethylcyclohexanecarboxamide

(72) (+)-Trans-N-(1-pivaloyloxymethyl-1H-pyrrolo[2,3-b]pyridin-4-yl)-4-(1-aminoethyl)cyclohexanecarboxamide

(73) Trans-N-(1-pivaloyloxymethyl-1H-pyrrolo[2,3-b]pyridin-4-yl)-4-(1-amino-1-methylethyl)cyclohexanecarboxamide

(74) Trans-N-(2-(4-methylphenylsulfonylamino)-4-pyridyl)-4-aminomethylcyclohexanecarboxamide

(75) Trans-N-(2-methoxycarbonylamino-4-pyridyl)-4-aminomethylcyclohexanecarboxamide

(76) (+)-Trans-N-(2-acetylamino-4-pyridyl)-4-(1-aminoethyl)cyclohexanecarboxamide

(77) Trans-N-(2-acetylamino-4-pyridyl)-4-(1-amino-1-methylethyl)cyclohexanecarboxamide

(78) (+)-Trans-N-(2-methylsulfonylamino-4-pyridyl)-4-(1-aminoethyl)cyclohexanecarboxamide

(79) Trans-N-(2-methylsulfonylamino-4-pyridyl)-4-(1-amino-1-methylethyl)cyclohexanecarboxamide

(80) (+)-Trans-N-(2-methylamino-4-pyridyl)-4-(1-aminoethyl)cyclohexanecarboxamide

(81) Trans-N-(2-methylamino-4-pyridyl)-4-(1-amino-1-methylethyl)cyclohexanecarboxamide

(82) (+)-Trans-N-(2-ethylamino-4-pyridyl)-4-(1-aminoethyl)cyclohexanecarboxamide

(83) Trans-N-(2-ethylamino-4-pyridyl)-4-(1-amino-1-methylethyl)cyclohexanecarboxamide
(84) Trans-N-(1H-pyrrolo[2,3-b]pyridin-4-yl)-cis-2-methyl-4-aminomethylcyclohexanecarboxamide
(85) Trans-N-(1H-pyrazolo[3,4-b]pyridin-4-yl)-cis-2-methyl-4-aminomethylcyclohexanecarboxamide

EXAMPLE 86

(a) Isothiourea sulfate (21.2 g) was dissolved in water (40 ml) and a 2N solution of sodium hydroxide (46 ml) was dropwise added under ice-cooling. The mixture was stirred at said temperature for 30 minutes and trans-4-aminomethylcyclohexanecarboxylic acid dissolved in boiling water (100 ml) was dropwise added and the mixture was stirred at room temperature for 24 hours. After completion of the reaction, the reaction mixture was cooled and the resultant crystals were collected by filtration. The crystals were thoroughly washed with cold water and dried to give 18.5 g of trans-4-guanidinomethylcyclohexanecarboxylic acid, melting point 325° C.

(b) To a solution of trans-4-guanidinomethylcyclohexanecarboxylic acid (82.36 g) dissolved in 1,2-dichloroethane (500 ml) were added diisopropylethylamine (210 ml) and chlorotrimethylsilane (153 ml). The mixture was stirred at 40° C. for 1.5 hours. After cooling, diisopropylethylamine (210 ml) and benzyl chloroformate (172 ml) were added thereto and the mixture was stirred under ice-cooling for 1 hour and at room temperature for 3 hours. The reaction mixture was adjusted to pH 2 with 1N hydrochloric acid and extracted with dichloromethane. The organic layer was concentrated under reduced pressure to give 202 g of red solids. The red solids were washed with dichloromethane and dried to give 125.9 g of pale yellow powdery trans-4-(1,3-dibenzyloxycarbonylguanidinomethyl)cyclohexanecarboxylic acid, melting point 140°–142° C.

(c) To a solution of trans-4-(1,3-dibenzyloxycarbonylguanidinomethyl)cyclohexanecarboxylic acid (60 g) dissolved in dichloromethane (300 ml) were added thionyl chloride (14 ml) and dimethylformamide (1 ml). The mixture was stirred at room temperature for 1 hour. The solvent was distilled away under reduced pressure to quantitatively give 63 g of trans-4-(1,3-dibenzyloxycarbonylguanidinomethyl)cyclohexanecarboxylic chloride as white crystals.

(d) To a solution of 4-amino-1H-pyrrolo[2,3-b]pyridine (2.46 g) dissolved in acetonitrile (100 ml) was added diisopropylethylamine (6.5 ml). The mixture was stirred at 40° C. Trans-4-(1,3-dibenzyloxycarbonylguanidinomethyl)cyclohexanecarboxylic chloride (19.86 g) was added to this solution and the mixture was stirred at 50° C. for 2 hours. Then, diisopropylethylamine (6 ml) and trans-4-(1,3-dibenzyloxycarbonylguanidinomethyl)cyclohexanecarboxylic chloride (15.03 g) were added thereto and the mixture was stirred at 50° C. for 2 hours. The solvent was distilled away under reduced pressure and the residue obtained was dissolved in methanol (100 ml). Sodium methoxide (1.05 g) was added to this solution and the mixture was stirred under ice-cooling for 1 hour and at room temperature for 1 hour. The solvent was distilled away under reduced pressure, chloroform (200 ml) was added thereto and the mixture was washed with water. The organic layer was dried over anhydrous sodium sulfate and concentrated under reduced pressure. The residue was purified by silica gel column chromatography to give 3.61 g of trans-N-(1H-pyrrolo[2,3-b]pyridin-4-yl)-4-(1-benzyloxycarbonylguanidinomethyl)cyclohexanecarboxamide, melting point 160°–162° C.

(e) Trans-N-(1H-pyrrolo[2,3-b]pyridin-4-yl)-4-(1-benzyloxyearbonylguanidinomethyl)cyclohexanecarboxamide (3.3 g) was dissolved in a mixed solvent of dioxane (100 ml) and dimethylformamide (50 ml), and 10% palladium hydroxide carbon (500 mg) was added thereto. A hydrogen gas was aerated and the mixture was stirred at 40° C. for 11 hours. The catalyst was filtered off and the filtrate was concentrated. The residue was dissolved in 15% hydrochloric acid-methanol and the solvent was concentrated under reduced pressure. The yellow solids obtained were recrystallized from ethyl acetate-methanol to give 1.5 g of trans-N-(1H-pyrrolo[2,3-b]pyridin-4-yl)-4-guanidinomethylcyclohexanecarboxamide dihydrochloride monohydrate, melting point 250° C. (decomposition).

EXAMPLE 87

(a) 4-Amino-1H-pyrazolo[2,3-b]pyridine dihydrochloride (3.3 g) was dissolved in dimethylformamide (30 ml) and acetonitrile (150 ml), and diisopropylethylamine (16.7 ml) was dropwise added thereto under ice-cooling. After stirring the mixture at said temperature for 30 minutes, a solution (50 ml) of trans-4-(1,3-dibenzyloxycarbonylguanidinomethyl)cyclohexanecarboxylic chloride (19.3 g) obtained in Example 86 (c) in acetonitrile was dropwise added thereto and the mixture was stirred at room temperature for 3 hours. After completion of the reaction, the solvent was distilled away under reduced pressure and the residue obtained was dissolved in methanol (100 ml). Sodium methoxide (860 mg) was added to this solution under ice-cooling and the mixture was stirred at room temperature for 1.5 hours. After completion of the reaction, the solvent was distilled away under reduced pressure and the reaction mixture was extracted with chloroform. The extract was washed with water, dried and concentrated under reduced pressure. The residue was purified by silica gel column chromatography to give 2.5 g of trans-N-(1H-pyrazolo[3,4-b]pyridin-4-yl)-4-(3-benzyloxycarbonylguanidinomethyl)cyclohexanecarboxamide.

PMR(DMSO-d$_6$/TMS) δ: 1.30–2.20(9H,m), 2.40(1H,m), 3.06(2H, br.d), 5.09(2H,s), 7.32(6H,br.s), 7.84(1H,d,J=5 Hz), 8.31(1H,s), 8.35(1H,d,J=5 Hz)

(b) Trans-N-(1H-pyrazolo[3,4-b]pyridin-4-yl)-4-(3-benzyloxycarbonylguanidinomethyl)cyclohexanecarboxamide (2.5 g) synthesized in Example 87 (a), 10% palladium hydroxide carbon (300 mg), dimethylformamide (10 ml) and methanol (60 ml) were placed in a 200 ml-autoclave and the mixture was stirred at initial hydrogen pressure of 10 atm and at 30°–40° C. for 1 hour. After completion of the reaction, the catalyst was filtered off and the filtrate was concentrated under reduced pressure. The obtained crystals were dissolved in methanol (10 ml) and 10% hydrochloric acid-methanol (5 ml) was added thereto under ice-cooling. The solvent was distilled away under reduced pressure and the crystals obtained were recrystallized from methanolethyl acetate-water to give 1.4 g of trans-N-(1H-pyrazolo[3,4-b]pyridin-4-yl)-4-guanidinomethylcyclohexanecarboxamide dihydrochloride monohydrate, melting point 260°–264° C.

The following compounds can be synthesized according to the method of the aforementioned Examples 86 or 87.
(88) Trans-N-(1H-pyrrolo[2,3-b]pyridin-4-yl)-4-guanidinomethylcyclohexanecarboxamide, m.p. 175° C. (decomposition)
(89) Trans-N-(1-methylpyrrolo[2,3-b]pyridin-4-yl)-4-(guanidinomethyl)cyclohexanecarboxamide dihydrochloride monohydrate, m.p. 236°–239° C.

(90) Trans-N-(1H-pyrrolo[2,3-b]pyridin-4-yl)-4-(2-imidazolin-2-yl)aminomethylcyclohexanecarboxamide
(91) Trans-N-(1H-pyrrolo[2,3-b]pyridin-4-yl)-4-(1-methylguanidinomethyl)cyclohexanecarboxamide
(92) Trans-N-(1H-pyrrolo[2,3-b]pyridin-4-yl)-4-(1-butylguanidinomethyl)cyclohexanecarboxamide
(93) Trans-N-(1H-pyrrolo[2,3-b]pyridin-4-yl)-4-(1,2-dimethylguanidinomethyl)cyclohexanecarboxamide
(94) Trans-N-(1H-pyrrolo[2,3-b]pyridin-4-yl)-4-(2-butyl-1-methylguanidinomethyl)cyclohexanecarboxamide
(95) Trans-N-(3-methyl-1H-pyrrolo[2,3-b]pyridin-4-yl)-4-guanidinomethylcyclohexanecarboxamide
(96) Trans-N-(1H-pyrazolo[3,4-b]pyridin-4-yl)-4-(2-imidazolin-2-yl)aminomethylcyclohexanecarboxamide
(97) Trans-N-(1H-pyrazolo[3,4-b]pyridin-4-yl)-4-(1-methylguanidinomethyl)cyclohexanecarboxamide
(98) Trans-N-(1H-pyrazolo[3,4-b]pyridin-4-yl)-4-(1-butylguanidinomethyl)cyclohexanecarboxamide
(99) Trans-N-(1H-pyrazolo[3,4-b]pyridin-4-yl)-4-(1,2-dimethylguanidinomethyl)cyclohexanecarboxamide
(100) Trans-N-(1-methylpyrazolo[3,4-b]pyridin-4-yl)-4-guanidinomethylcyclohexanecarboxamide
(101) Trans-N-(1-benzyloxymethylpyrrolo[2,3-b]pyridin-4-yl)-4-guanidinomethylcyclohexanecarboxamide, m.p. 190°–192° C.
(102) Trans-N-(1-methoxymethylpyrrolo[2,3-b]pyridin-4-yl)-4-guanidinomethylcyclohexanecarboxamide
(103) Trans-N-(1-hydroxymethylpyrrolo[2,3-b]pyridin-4-yl)-4-guanidinomethylcyclohexanecarboxamide
(104) Trans-N-(1-(2,3,4,5-tetrahydrofuran-2-yl)pyrrolo[2,3-b]pyridin-4-yl)-4-guanidinomethylcyclohexanecarboxamide
(105) Trans-N-(1-dimethylcarbamoylpyrrolo[2,3-b]pyridin-4-yl)-4-guanidinomethylcyclohexanecarboxamide
(106) Trans-N-(1-acetylpyrrolo[2,3-b]pyridin-4-yl)-4-guanidinomethylcyclohexanecarboxamide
(107) N$^1$-[trans-(4-(1H-pyrrolo[2,3-b]pyridin-4-yl)carbamoyl)cyclohexylmethyl]formamidine
(108) N$^1$-[trans-(4-(1H-pyrrolo[2,3-b]pyridin-4-yl)carbamoyl)cyclohexylmethyl]acetamidine
(109) Trans-N-(1H-pyrrolo[2,3-b]pyridin-4-yl)-4-(2-nitroguanidinomethyl)cyclohexanecarboxamide
(110) Trans-N-(1H-pyrrolo[2,3-b]pyridin-4-yl)-4-(2-cyanoguanidinomethyl)cyclohexanecarboxamide
(111) Trans-N-(1H-pyrrolo[2,3-b]pyridin-4-yl)-4-(1,2-dibenzylguanidinomethyl)cyclohexanecarboxamide
(112) Trans-N-(1-benzylpyrrolo[2,3-b]pyridin-4-yl)-4-guanidinomethylcyclohexanecarboxamide
(113) Trans-N-(1-(p-methoxybenzyl)pyrrolo[2,3-b]pyridin-4-yl)-4-guanidinomethylcyclohexanecarboxamide
(114) Trans-N-(3-formyl-1H-pyrrolo[2,3-b]pyridin-4-yl)-4-guanidinomethylcyclohexanecarboxamide
(115) Trans-N-(3-methoxycarbonyl-1H-pyrrolo[2,3-b]pyridin-4-yl)-4-guanidinomethylcyclohexanecarboxamide
(116) Trans-N-(2,3-dihydro-2-oxo-1H-pyrrolo[2,3-b]pyridin-4-yl)-4-guanidinomethylcyclohexanecarboxamide
(117) Trans-N-(2-chloro-1H-pyrrolo[2,3-b]pyridin-4-yl)-4-guanidinomethylcyclohexanecarboxamide
(118) Trans-N-(1H-pyrazolo[3,4-b]pyridin-4-yl)-4-(2-nitroguanidinomethyl)cyclohexanecarboxamide
(119) Trans-N-(1H-pyrazolo[3,4-b]pyridin-4-yl)-4-(2-cyanoguanidinomethyl)cyclohexanecarboxamide
(120) Trans-N-(1H-pyrazolo[3,4-b]pyridin-4-yl)-4-(1,2-dibenzylguanidinomethyl)cyclohexanecarboxamide
(121) Trans-N-(1-benzylpyrazolo[3,4-b]pyridin-4-yl)-4-guanidinomethylcyclohexanecarboxamide
(122) Trans-N-(1-(p-methoxybenzyl)pyrazolo[3,4-b]pyridin-4-yl)-4-guanidinomethylcyclohexanecarboxamide
(123) Trans-N-(3-carboxy-1H-pyrrolo[2,3-b]pyridin-4-yl)-4-guanidinomethylcyclohexanecarboxamide
(124) Trans-N-(3-cyano-1H-pyrrolo[2,3-b]pyridin-4-yl)-4-guanidinomethylcyclohexanecarboxamide
(125) Trans-N-(2,3-dihydro-2,3-dioxo-1H-pyrrolo[2,3-b]pyridin-4-yl)-4-guanidinomethylcyclohexanecarboxamide
(126) Trans-N-(2,3-dihydro-1H-pyrrolo[2,3-b]pyridin-4-yl)-4-guanidinomethylcyclohexanecarboxamide
(127) Trans-N-(2-amino-4-pyridyl)-4-guanidinomethylcyclohexanecarboxamide dihydrochloride monohydrate, m.p. 240° C. (decomposition)
(128) Trans-N-(1-benzyloxymethyl-1H-pyrrolo[2,3-b]pyridin-4-yl)-4-(2-imidazolin-2-yl)aminomethylcyclohexanecarboxamide, m.p. 211°–212° C.
(129) Trans-N-(1H-pyrrolo[2,3-b]pyridin-4-yl)-cis-2-methyl-4-guanidinomethylcyclohexanecarboxamide
(130) Trans-N-(1H-pyrazolo[3,4-b]pyridin-4-yl)-cis-2-methyl-4-guanidinomethylcyclohexanecarboxamide
(131) (+)-Trans-N-(1H-pyrrolo[2,3-b]pyridin-4-yl)-4-(1-methyl-1-guanidinoethyl)cyclohexanecarboxamide
(132) Trans-N-(1H-pyrrolo[2,3-b]pyridin-4-yl)-4-(1,1-dimethylguanidinomethyl)cyclohexanecarboxamide
(133) (+)-Trans-N-(1H-pyrazolo[3,4-b]pyridin-4-yl)-4-(1-methyl-1-guanidinoethyl)cyclohexanecarboxamide
(134) Trans-N-(1H-pyrazolo[3,4-b]pyridin-4-yl)-4-(1,1-dimethylguanidinomethyl)cyclohexanecarboxamide
(135) Trans-N-(2-ethylcarbamoyl-4-pyridyl)-4-aminomethylcyclohexanecarboxamide
(136) (+)-Trans-N-(2-ethylcarbamoyl-4-pyridyl)-4-(1-aminoethyl)cyclohexanecarboxamide
(137) Trans-N-(2-ethylcarbamoyl-4-pyridyl)-4-(1-amino-1-methylethyl)cyclohexanecarboxamide Formulation Example 1: Tablets

| Compound of the Invention | 10.0mg |
|---|---|
| Lactose | 50.0mg |
| Corn starch | 20.0mg |
| Crystalline cellulose | 29.7mg |
| Polyvinylpyrrolidone K30 | 5.0mg |
| Talc | 5.0mg |
| Magnesium stearate | 0.3mg |
| | 120.0mg |

The compound of the present invention, lactose, corn starch and crystalline cellulose were mixed and kneaded by the use of polyvinylpyrrolidone K30 paste. The mixture was granulated by passing through a sieve of 20 mesh. After being dried at 50° C. for 2 hours, the granules are passed through a 24 mesh sieve, admixed with talc and magnesium stearate and prepared into 120 mg each tablet with a 7 mm-diameter pounder.

Formulation Example 2: Capsules

| Compound of the Invention | 10.0mg |
|---|---|
| Lactose | 70.0mg |
| Corn starch | 35.0mg |
| Polyvinylpyrrolidone K30 | 2.0mg |
| Talc | 2.7mg |
| Magnesium stearate | 0.3mg |
| | 120.0mg |

The compound of the present invention, lactose, and corn starch were mixed and kneaded by the use of polyvinylpyrrolidone K30 paste. The mixture was granulated by passing through a sieve of 20 mesh. After being dried at 50° C. for 2 hours, the granules are passed through a 24 mesh sieve, admixed with talc and magnesium stearate and filled in a hard capsule (grade 4) to give a 120 mg capsule.

What is claimed is:

1. A 4-amino(alkyl)cyclohexane-1-carboxamide compound of the formula (I)

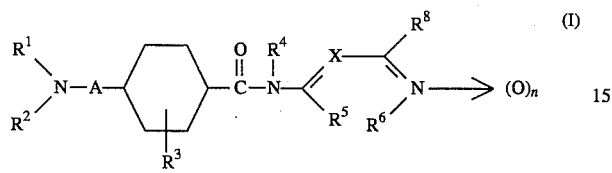

wherein:

$R^1$ and $R^2$ are the same or different and each is hydrogen, alkyl, or cycloalkyl, cycloalkylalkyl, phenyl, aralkyl, piperidyl or pyrrolidinyl, which may have substituent on the ring, or a group of the formula

wherein

R is hydrogen, alkyl, —NR'R" (where R' and R" are the same or different and each is hydrogen, alkyl, aralkyl or phenyl), $R^0$ is hydrogen, alkyl, aralkyl, phenyl, nitro or cyano, or R and $R^0$ may combinedly form a heterocyclic ring which may have, in the ring, oxygen atom, sulfur atom or optionally substituted nitrogen atom, or $R^1$ and $R^2$ combinedly are alkylidene or phenylalkylidene, or $R^1$ and $R^2$ form, together with the nitrogen atom binding therewith, a heterocyclic ring which may have, in the ring, oxygen atom, sulfur atom or optionally substituted nitrogen atom;

$R^3$ and $R^4$ are each hydrogen or alkyl;

A is a single bond or alkylene;

X is =C($R^7$)— or =N—;

$R^5$ and $R^6$ together are a group of the formula

—CRa=CRb—, (a)

—NRa—C(=Rb)— or (b)

—C(=Ra)—NRb—, (d)

wherein

Ra and Rb combinedly form an optionally hydrogenated 5- or 6-membered aromatic ring which may have, in the ring, at least one of nitrogen atom, sulfur atom and oxygen atom;

$R^7$ and $R^8$ are the same or different and each is hydrogen, halogen, alkyl, alkoxy, aralkyl, haloalkyl, nitro, —NReRf {wherein Re and Rf are the same or different and each is hydrogen, alkyl, —COR$^9$, —COOR$^{9'}$, —SO$_2$R$^{9'}$ (where R$^9$ is hydrogen, alkyl, phenyl or aralkyl and R$^{9'}$ is alkyl, phenyl or aralkyl), or Re and Rf form, together with the nitrogen atom binding therewith, a heterocyclic ring which may have, in the ring, oxygen atom, sulfur atom or optionally substituted nitrogen atom}, cyano, azido, optionally substituted hydrazino, —COOR$^{10}$, —CONR$^{11}$R$^{12}$ (wherein R$^{10-12}$ are each hydrogen, alkyl, phenyl or aralkyl); and n is 0 or 1;

an isomer thereof or a pharmaceutically acceptable acid addition salt thereof.

2. The 4-amino(alkyl)cyclohexane-1-carboxamide compound of claim 1, having the formula (Ia)

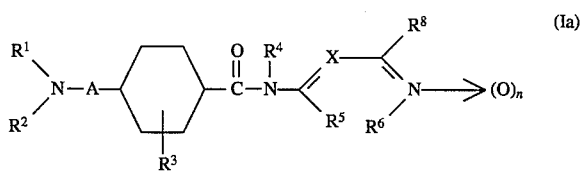

wherein:

$R^1$ and $R^2$ are the same or different and each is hydrogen, alkyl having 1 to 10 carbon atoms, or cycloalkyl having 3 to 7 carbon atoms, cycloalkylalkyl, phenyl, aralkyl, piperidyl or pyrrolidinyl which may have substituent on the ring, or $R^1$ and $R^2$ combinedly are alkylidene or phenylalkylidene, or $R^1$ and $R^2$ form, together with the nitrogen atom binding therewith, a heterocyclic ring which may have, in the ring, oxygen atom, sulfur atom or optionally substituted nitrogen atom;

$R^3$ and $R^4$ are each hydrogen or alkyl;

A is a single bond or alkylene;

X is =C($R^7$)— or =N—;

$R^5$ and $R^6$ together are a group of the formula

| —CRa=CRb— | (a), | —NRa—C(=Rb)— | (b) or |
|---|---|---|---|
|  |  | —C(=Ra)—NRb— | (d), | wherein

Ra and Rb combinedly form an optionally hydrogenated 5- or 6-membered aromatic ring which may have, in the ring, at least one of nitrogen atom, sulfur atom and oxygen atom;

$R^7$ and $R^8$ are the same or different and each is hydrogen, halogen, alkyl, alkoxy, aralkyl, haloalkyl, nitro, —NReRf {wherein Re and Rf are the same or different are each is hydrogen, alkyl, —COR$^9$, —COOR$^{9'}$ or —SO$_2$R$^{9'}$ (where R$^9$ is hydrogen, alkyl, phenyl or aralkyl and R$^{9'}$ is alkyl, phenyl or aralkyl), or Re and Rf form, together with the nitrogen atom binding therewith, a heterocyclic ring which may have, in the ring, oxygen atom, sulfur atom or optionally substituted nitrogen atom}, cyano, azido, optionally substituted hydrazino, —COOR$^{10}$, —CONR$^{11}$R$^{12}$ (wherein R$^{10-12}$ are each hydrogen, alkyl, phenyl or aralkyl); and n is 0 or 1;

an isomer thereof or a pharmaceutically acceptable acid addition salt thereof.

3. The 4-amino(alkyl)cyclohexane-1-carboxamide compound of claim 1, having the formula (Ib)

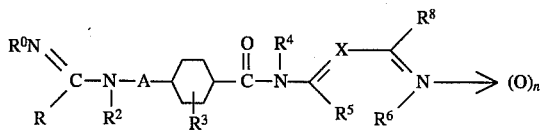

wherein:
R is hydrogen, alkyl or —NR'R" (wherein R' and R" are the same or different and each is hydrogen, alkyl, aralkyl or phenyl);
$R^0$ is hydrogen, alkyl, aralkyl, phenyl, nitro or cyano, or R and $R^0$ combinedly form a heterocyclic ring which may have, in the ring, oxygen atom, sulfur atom or optionally substituted nitrogen atom;
$R^2$ is hydrogen, alkyl or aralkyl;
$R^3$ and $R^4$ are each hydrogen or alkyl;
A is a single bond or alkylene;
X is $=C(R^7)$— or $=N$—;
$R^5$ and $R^6$ together are a group of the formula

| —CRa=CRb— | (a), | —NRa—C(=Rb)— | (b) or |
|---|---|---|---|
| | | —C(=Ra)—NRb— | (d), | wherein
Ra and Rb combinedly form an optionally hydrogenated 5- or 6-membered aromatic
$R^7$ and $R^8$ are the same or different and each is hydrogen, halogen, alkyl, alkoxy, aralkyl, haloalkyl, nitro, —NReRf {wherein Re and Rf are the same or different are each is hydrogen, alkyl, —$COR^9$, —$COOR^{9'}$ or —$SO_2R^{9'}$ (where $R^9$ is hydrogen, alkyl, phenyl or aralkyl and $R^{9'}$ is alkyl, phenyl or aralkyl), or Re and Rf form, together with the nitrogen atom binding therewith, a heterocyclic ring which may have, in the ring, oxygen atom, sulfur atom or optionally substituted nitrogen atom}, cyano, azido, optionally substituted hydrazino, —$COOR^{10}$, —$CONR^{11}R^{12}$ (wherein $R^{10-12}$ are each hydrogen, alkyl, phenyl or aralkyl); and
n is 0 or 1;
an isomer thereof or a pharmaceutically acceptable acid addition salt thereof.

4. The compound of claim 1, which is selected from the group consisting of:
trans-N-(1H-pyrrolo[2,3-b]pyridin-4-yl)-4-aminomethylcyclohexanecarboxamide,
trans-N-(1H-pyrazolo[3,4-b]pyridin-4-yl)-4-aminomethylcyclohexanecarboxamide,
(+)-trans-N-(1H-pyrrolo[2,3-b]pyridin-4-yl)-4-(1-aminoethyl)cyclohexanecarboxamide,
trans-N-(1H-pyrrolo[2,3-b]pyridin-4-yl)-4-(1-amino-1-methylethyl)cyclohexanecarboxamide,
(+)-trans-N-(1H-pyrazolo[3,4-b]pyridin-4-yl)-4-(1-aminoethyl)cyclohexanecarboxamide,
trans-N-(1H-pyrazolo[3,4-b]pyridin-4-yl)-4-(1-amino-1-methylethyl)cyclohexanecarboxamide,
(+)-trans-N-(2,3-dihydro-1H-pyrrolo[2,3-b]pyridin-4-yl)-4-(1-aminoethyl)cyclohexanecarboxamide,
(+)-trans-N-(2,3-dihydro-2-oxo-1H-pyrrolo[2,3-b]pyridin-4-yl)-4-(1-aminoethyl)cyclohexanecarboxamide,
an isomer thereof or a pharmaceutically acceptable acid addition salt thereof.

5. The compound of claim 1, which is selected from the group consisting of:
trans-N-(1H-pyrrolo[2,3-b]pyridin-4-yl)-4-guanidinomethylcyclohexanecarboxamide,
trans-N-(1H-pyrazolo[3,4-b]pyridin-4-yl)-4-guanidinomethylcyclohexanecarboxamide,
trans-N-(1H-pyrrolo[2,3-b]pyridin-4-yl)-4-(2-imidazolin-2-yl)aminomethylcyclohexanecarboxamide,
trans-N-(1H-pyrrolo[2,3-b]pyridin-4-yl)-4-(1-methylguanidinomethyl)cyclohexanecarboxamide,
N'-[trans-(4-(1H-pyrrolo[2,3-b]pyridin-4-yl)carbamoyl)cyclohexylmethyl]formamidine,
trans-N-(2,3-dihydro-2-oxo-1H-pyrrolo[2,3-b]pyridin-4-yl)-4-guanidinomethylcyclohexanecarboxamide, and
trans-N-(2,3-dihydro-1H-pyrrolo[2,3-b]pyridin-4-yl)-4-guanidinomethylcyclohexanecarboxamide, an isomer thereof or a pharmaceutically acceptable acid addition salt thereof.

6. A pharmaceutical composition comprising, as an active ingredient, a 4-amino(alkyl)cyclohexane-1-carboxamide compound as claimed in any one of claim 1 to claim 5, an isomer thereof or a pharmaceutically acceptable acid addition salt thereof, and a pharmaceutically acceptable additive.

7. An antihypertensive agent comprising, as an active ingredient, a 4-amino(alkyl)cyclohexane-1-carboxamide compound as claimed in any one of claim 1 to claim 5, an isomer thereof or a pharmaceutically acceptable acid addition salt thereof, and a pharmaceutically acceptable additive.

8. A therapeutic agent for angina pectoris, comprising, as an active ingredient, a 4-amino(alkyl)cyclohexane-1-carboxamide compound as claimed in any one of claim 1 to claim 5, an isomer thereof or a pharmaceutically acceptable acid addition salt thereof, and a pharmaceutically acceptable additive.

9. A therapeutic agent for asthma, comprising, as an active ingredient, a 4-amino(alkyl)cyclohexane-1-carboxamide compound as claimed in any one of claim 1 to claim 5, an isomer thereof or a pharmaceutically acceptable acid addition salt thereof, and a pharmaceutically acceptable additive.

10. An agent for improving peripheral circulation, comprising, as an active ingredient, a 4-amino(alkyl)cyclohexane-1-carboxamide compound as claimed in any one of claim 1 to claim 5, an isomer thereof or a pharmaceutically acceptable acid addition salt thereof, and a pharmaceutically acceptable additive.

* * * * *

UNITED STATES PATENT AND TRADEMARK OFFICE
CERTIFICATE OF CORRECTION

PATENT NO. : 5,478,838
DATED : December 26, 1995
INVENTOR(S) : Masafumi ARITA, Tadamasa SAITO, Hirofumi OKUDA, Hiroyuki SATO and Masayoshi UEHATA

It is certified that error appears in the above-indentified patent and that said Letters Patent is hereby corrected as shown below:

COLUMN 39:

Claim 3, line 17 from the bottom, after "aromatic", insert --ring which may have, in the ring, at least one of nitrogen atom, sulfur atom and oxygen atom;--.

Signed and Sealed this

Eleventh Day of June, 1996

Attest:

BRUCE LEHMAN

Attesting Officer

Commissioner of Patents and Trademarks